(12) United States Patent
Clark et al.

(10) Patent No.: US 11,307,190 B2
(45) Date of Patent: Apr. 19, 2022

(54) SYSTEMS FOR MEASURING PROPERTIES OF WATER IN A WATER DISTRIBUTION SYSTEM

(71) Applicant: Mueller International, LLC, Atlanta, GA (US)

(72) Inventors: Kenneth A. Clark, Chattanooga, TN (US); Timofey Sitnikov, Harrison, TN (US); Paul Gifford, Chattanooga, TN (US)

(73) Assignee: Mueller International, LLC, Atlanta, GA (US)

( * ) Notice: Subject to any disclaimer, the term of this patent is extended or adjusted under 35 U.S.C. 154(b) by 0 days.

(21) Appl. No.: 16/118,664

(22) Filed: Aug. 31, 2018

(65) Prior Publication Data

US 2018/0372706 A1  Dec. 27, 2018

Related U.S. Application Data

(62) Division of application No. 14/209,257, filed on Mar. 13, 2014, now Pat. No. 10,180,414.
(Continued)

(51) Int. Cl.
*G01N 33/18* (2006.01)
*F17D 5/00* (2006.01)
(Continued)

(52) U.S. Cl.
CPC ............ *G01N 33/18* (2013.01); *F17D 5/00* (2013.01); *E03B 7/071* (2013.01); *E03F 3/04* (2013.01);
(Continued)

(58) Field of Classification Search
None
See application file for complete search history.

(56) References Cited

U.S. PATENT DOCUMENTS 1,661,265 A * 3/1928 Olbricht ................. F01K 11/02
261/118
1,788,618 A   1/1931 Cover
(Continued)

FOREIGN PATENT DOCUMENTS

AU  2009308949  5/2010
AU  2010249499  5/2015
(Continued)

OTHER PUBLICATIONS

US 10,101,311 B2, 10/2018, Clark et al. (withdrawn)
(Continued)

*Primary Examiner* — Arleen M Vazquez
*Assistant Examiner* — Leonard S Liang
(74) *Attorney, Agent, or Firm* — Taylor English Duma LLP

(57) ABSTRACT

Systems and methods of measuring properties of water in a water distribution system are provided. An analysis system, according to one embodiment, comprises a plurality of water sensors connected at various points to the water distribution system, each of the plurality of water sensors configured to measure a property of water. The analysis system also includes a computer server configured to communicate with the plurality of water sensors via a network and receive water measurement data from the plurality of water sensors. The computer server comprises a processor, a database configured to store the water measurement data, and a system health monitoring module configured to evaluate the health of the water distribution system to obtain health data. The analysis system further includes at least one client device configured to communicate with the computer server via the network and receive the health data from the computer server.

16 Claims, 20 Drawing Sheets

Related U.S. Application Data

(60) Provisional application No. 61/794,616, filed on Mar. 15, 2013.

(51) Int. Cl.

| | | |
|---|---|---|
| G05B 15/02 | (2006.01) | |
| E03B 7/07 | (2006.01) | |
| G08B 21/18 | (2006.01) | |
| G01F 15/063 | (2022.01) | |
| G01M 3/00 | (2006.01) | |
| G06F 3/0484 | (2022.01) | |
| G01M 3/24 | (2006.01) | |
| E03F 3/04 | (2006.01) | |
| G06Q 50/06 | (2012.01) | |
| H04Q 9/00 | (2006.01) | |

(52) U.S. Cl.
CPC ............ *G01F 15/063* (2013.01); *G01M 3/00* (2013.01); *G01M 3/243* (2013.01); *G05B 15/02* (2013.01); *G06F 3/0484* (2013.01); *G06Q 50/06* (2013.01); *G08B 21/18* (2013.01); *H04Q 9/00* (2013.01); *Y10T 137/7025* (2015.04)

(56) References Cited

U.S. PATENT DOCUMENTS

| | | | |
|---|---|---|---|
| 1,901,772 A * | 3/1933 | Pfau | F03B 15/10 |
| | | | 91/47 |
| 2,099,479 A | 11/1937 | Heinkel | |
| 2,336,450 A * | 12/1943 | Voorhess | F03B 15/12 |
| | | | 415/49 |
| 2,524,031 A * | 10/1950 | Arps | E21B 47/18 |
| | | | 324/356 |
| 2,828,762 A | 4/1958 | Swank | |
| 2,931,383 A | 4/1960 | Harold | |
| 3,047,079 A * | 7/1962 | Wepsala, Jr. | E21B 4/02 |
| | | | 175/107 |
| 3,077,937 A * | 2/1963 | Tiraspolsky | E21B 4/02 |
| | | | 175/107 |
| 3,084,515 A * | 4/1963 | Dougherty | B65G 5/00 |
| | | | 405/53 |
| 3,128,998 A * | 4/1964 | Sibley | E21C 27/24 |
| | | | 299/37.1 |
| 3,391,735 A * | 7/1968 | Schramm | E21B 7/12 |
| | | | 166/359 |
| 3,404,738 A * | 10/1968 | Lindquist | F03B 11/00 |
| | | | 416/146 R |
| 3,602,603 A * | 8/1971 | Fukasu | F03B 15/14 |
| | | | 415/38 |
| 3,705,385 A | 12/1972 | Batz | |
| 4,039,784 A | 8/1977 | Quarton | |
| 4,093,997 A | 6/1978 | Germer | |
| 4,120,031 A | 10/1978 | Kincheloe et al. | |
| 4,149,676 A * | 4/1979 | Wieck | A01G 25/097 |
| | | | 239/210 |
| 4,282,413 A | 8/1981 | Simons | |
| 4,291,375 A | 9/1981 | Wolf | |
| 4,388,690 A | 6/1983 | Lumsden | |
| 4,414,633 A | 11/1983 | Churchill | |
| 4,442,492 A | 4/1984 | Karlsson et al. | |
| 4,465,970 A | 8/1984 | Dimassimo et al. | |
| 4,491,186 A * | 1/1985 | Alder | E21B 19/08 |
| | | | 173/9 |
| 4,516,213 A | 5/1985 | Gidden | |
| 4,520,516 A * | 6/1985 | Parsons | E03C 1/057 |
| | | | 251/129.03 |
| 4,542,469 A | 9/1985 | Brandberry et al. | |
| 4,591,988 A | 5/1986 | Klima et al. | |
| 4,674,279 A * | 6/1987 | Ali | F03B 15/14 |
| | | | 290/43 |
| 4,705,060 A | 11/1987 | Goulbourne | |
| 4,707,852 A | 11/1987 | Jahr et al. | |
| 4,727,900 A | 3/1988 | Dooling et al. | |
| 4,792,946 A | 12/1988 | Mayo | |
| 4,803,632 A | 2/1989 | Frew et al. | |
| 4,833,618 A | 5/1989 | Verma et al. | |
| 4,868,566 A | 9/1989 | Strobel et al. | |
| 4,881,070 A | 11/1989 | Burrowes et al. | |
| 4,940,976 A | 7/1990 | Gastouniotis et al. | |
| 4,945,344 A | 7/1990 | Farrell | |
| 4,989,830 A | 2/1991 | Ratnik | |
| 5,006,240 A | 4/1991 | Steffero, Sr. | |
| 5,056,107 A | 10/1991 | Johnson et al. | |
| 5,075,792 A | 12/1991 | Brown et al. | |
| 5,079,715 A | 1/1992 | Venkataraman et al. | |
| 5,095,705 A * | 3/1992 | Daly | F03G 3/00 |
| | | | 60/641.2 |
| 5,121,344 A | 6/1992 | Laage et al. | |
| 5,239,575 A | 8/1993 | White et al. | |
| 5,298,894 A | 3/1994 | Cerny | |
| 5,327,925 A | 7/1994 | Ortel | |
| 5,381,136 A | 1/1995 | Powers et al. | |
| 5,434,911 A | 7/1995 | Gray et al. | |
| 5,438,329 A | 8/1995 | Gastouniotis et al. | |
| 5,451,938 A | 9/1995 | Brennan, Jr. | |
| 5,459,459 A | 10/1995 | Lee, Jr. | |
| 5,481,259 A | 1/1996 | Bane | |
| 5,493,287 A | 2/1996 | Bane | |
| 5,525,898 A | 6/1996 | Lee et al. | |
| 5,553,094 A | 9/1996 | Johnson et al. | |
| 5,588,462 A | 12/1996 | Mchugh | |
| 5,590,179 A | 12/1996 | Shincovich et al. | |
| 5,594,740 A | 1/1997 | Ladue | |
| 5,617,084 A | 4/1997 | Sears | |
| 5,631,554 A | 5/1997 | Briese et al. | |
| 5,634,488 A | 6/1997 | Martin, Jr. | |
| 5,646,863 A | 7/1997 | Morton | |
| 5,654,692 A | 8/1997 | Baxter, Jr. et al. | |
| 5,673,252 A | 9/1997 | Johnson et al. | |
| 5,708,195 A | 1/1998 | Kurisu et al. | |
| 5,714,931 A | 2/1998 | Petite | |
| 5,748,104 A | 5/1998 | Argyroudis et al. | |
| 5,751,797 A | 5/1998 | Saadeh | |
| 5,757,357 A | 5/1998 | Grande et al. | |
| 5,801,643 A | 9/1998 | Williams et al. | |
| 5,815,086 A | 9/1998 | Ivie et al. | |
| 5,839,508 A * | 11/1998 | Tubel | G01V 1/42 |
| | | | 166/65.1 |
| 5,852,658 A | 12/1998 | Knight et al. | |
| 5,877,703 A | 3/1999 | Bloss et al. | |
| 5,892,758 A | 4/1999 | Argyroudis | |
| 5,901,738 A | 5/1999 | Miller | |
| 5,907,491 A | 5/1999 | Canada et al. | |
| 5,924,051 A | 7/1999 | Provost et al. | |
| 5,926,103 A | 7/1999 | Petite | |
| 5,926,531 A | 7/1999 | Petite | |
| 5,940,009 A | 8/1999 | Loy et al. | |
| 5,963,146 A | 10/1999 | Johnson et al. | |
| 5,971,011 A | 10/1999 | Price | |
| 5,993,739 A | 11/1999 | Lyon | |
| 5,994,892 A | 11/1999 | Turing et al. | |
| 6,006,212 A | 12/1999 | Schleich et al. | |
| 6,028,522 A | 2/2000 | Petite | |
| 6,031,455 A | 2/2000 | Grube et al. | |
| 6,036,401 A | 3/2000 | Morina et al. | |
| 6,044,062 A | 3/2000 | Brownrigg et al. | |
| 6,058,374 A | 5/2000 | Guthrie et al. | |
| 6,060,994 A | 5/2000 | Chen | |
| 6,078,269 A | 6/2000 | Markwell | |
| 6,081,204 A | 6/2000 | Lavoie et al. | |
| 6,163,276 A | 12/2000 | Irving et al. | |
| 6,172,616 B1 | 1/2001 | Johnson et al. | |
| 6,194,902 B1 | 2/2001 | Kuo | |
| 6,195,018 B1 | 2/2001 | Ragle et al. | |
| 6,218,953 B1 | 4/2001 | Petite | |
| 6,233,327 B1 | 5/2001 | Petite | |
| 6,246,677 B1 | 6/2001 | Nap et al. | |
| 6,249,516 B1 | 6/2001 | Brownrigg et al. | |
| 6,288,641 B1 | 9/2001 | Casais | |
| 6,317,051 B1 | 11/2001 | Cohen | |

(56) References Cited

U.S. PATENT DOCUMENTS

| | | | |
|---|---|---|---|
| 6,333,975 B1 | 12/2001 | Brunn et al. |
| 6,356,205 B1 | 3/2002 | Salvo et al. |
| 6,373,399 B1 | 4/2002 | Johnson et al. |
| 6,392,538 B1 | 5/2002 | Shere |
| 6,424,270 B1 | 7/2002 | Ali |
| 6,430,268 B1 | 8/2002 | Petite |
| 6,437,692 B1 | 8/2002 | Petite et al. |
| 6,453,247 B1 | 9/2002 | Hunaidi |
| 6,456,197 B1 | 9/2002 | Lauritsen et al. |
| 6,470,903 B2 | 10/2002 | Reyman |
| 6,487,457 B1 | 11/2002 | Hull et al. |
| 6,493,377 B2 | 12/2002 | Schilling et al. |
| 6,512,463 B1 | 1/2003 | Campbell et al. |
| 6,528,957 B1 | 3/2003 | Luchaco |
| 6,538,577 B1 | 3/2003 | Ehrke et al. |
| 6,560,543 B2 | 5/2003 | Wolfe et al. |
| 6,564,159 B1 | 5/2003 | Lavoie et al. |
| 6,577,961 B1 | 6/2003 | Hubbard et al. |
| 6,618,578 B1 | 9/2003 | Petite |
| 6,624,750 B1 | 9/2003 | Marman et al. |
| 6,628,207 B1 | 9/2003 | Hemminger et al. |
| 6,628,764 B1 | 9/2003 | Petite |
| 6,633,781 B1 | 10/2003 | Lee et al. |
| 6,653,945 B2 | 11/2003 | Johnson et al. |
| 6,657,552 B2 | 12/2003 | Belski et al. |
| 6,675,071 B1 | 1/2004 | Griffin, Jr. et al. |
| 6,675,834 B1 | 1/2004 | Lai |
| 6,677,861 B1 | 1/2004 | Henry et al. |
| 6,710,721 B1 | 3/2004 | Holowick |
| 6,747,557 B1 | 6/2004 | Petite et al. |
| 6,798,352 B2 | 9/2004 | Holowick |
| 6,816,072 B2 | 11/2004 | Zoratti |
| 6,830,061 B2 | 12/2004 | Adams et al. |
| 6,836,737 B2 | 12/2004 | Petite et al. |
| 6,847,300 B2 | 1/2005 | Yee et al. |
| 6,876,100 B2 | 4/2005 | Yumita |
| 6,891,477 B2 | 5/2005 | Aronstam |
| 6,891,838 B1 | 5/2005 | Petite et al. |
| 6,914,533 B2 | 7/2005 | Petite |
| 6,914,893 B2 | 7/2005 | Petite |
| 6,931,445 B2 | 8/2005 | Davis |
| 6,946,972 B2 | 9/2005 | Mueller et al. |
| 6,954,701 B2 | 10/2005 | Wolfe |
| 6,954,814 B1 | 10/2005 | Leach |
| 6,963,808 B1 | 11/2005 | Addink et al. |
| 6,963,817 B2 | 11/2005 | Ito et al. |
| 6,970,808 B2 | 11/2005 | Abhulimen et al. |
| 6,972,677 B2 | 12/2005 | Coulthard |
| 6,978,210 B1 | 12/2005 | Suter et al. |
| 6,980,079 B1 | 12/2005 | Shintani |
| 6,998,724 B2 * | 2/2006 | Johansen | E21B 33/0355 |
| | | | 166/65.1 |
| 7,002,481 B1 | 2/2006 | Crane et al. |
| 7,008,239 B1 | 3/2006 | Ju |
| 7,009,530 B2 | 3/2006 | Zigdon et al. |
| 7,012,546 B1 | 3/2006 | Zigdon et al. |
| 7,020,701 B1 | 3/2006 | Gelvin |
| 7,042,368 B2 | 5/2006 | Patterson et al. |
| 7,053,767 B2 | 5/2006 | Petite et al. |
| 7,054,271 B2 | 5/2006 | Brownrigg |
| 7,061,924 B1 | 6/2006 | Durrant et al. |
| 7,072,945 B1 | 7/2006 | Nieminen et al. |
| 7,079,810 B2 | 7/2006 | Petite et al. |
| 7,088,239 B2 | 8/2006 | Basinger et al. |
| 7,089,125 B2 | 8/2006 | Sonderegger |
| 7,103,511 B2 | 9/2006 | Petite |
| 7,117,051 B2 | 10/2006 | Landry et al. |
| 7,124,184 B2 | 10/2006 | Chung et al. |
| 7,137,550 B1 | 11/2006 | Petite |
| 7,142,107 B2 | 11/2006 | Kates |
| 7,201,180 B2 | 4/2007 | Ephrat et al. |
| 7,219,553 B1 | 5/2007 | Worthington |
| 7,248,181 B2 | 7/2007 | Patterson et al. |
| 7,252,431 B1 * | 8/2007 | Caramanna | G01K 1/14 |
| | | | 116/216 |
| 7,253,536 B2 | 8/2007 | Fujimoto et al. |
| 7,256,704 B2 | 8/2007 | Yoon et al. |
| 7,263,073 B2 | 8/2007 | Petite et al. |
| 7,290,450 B2 | 11/2007 | Brown et al. |
| 7,292,143 B2 | 11/2007 | Drake et al. |
| 7,295,128 B2 | 11/2007 | Petite |
| 7,301,456 B2 | 11/2007 | Han |
| 7,310,590 B1 | 12/2007 | Bansal |
| 7,315,257 B2 | 1/2008 | Patterson et al. |
| 7,330,796 B2 | 2/2008 | Addink et al. |
| 7,342,504 B2 | 3/2008 | Crane et al. |
| 7,353,280 B2 | 4/2008 | Chiles et al. |
| 7,356,614 B2 | 4/2008 | Kim et al. |
| 7,363,031 B1 | 4/2008 | Aisa |
| 7,397,907 B2 | 7/2008 | Petite |
| 7,417,557 B2 | 8/2008 | Osterloh et al. |
| 7,423,985 B1 | 9/2008 | Hill |
| 7,424,527 B2 | 9/2008 | Petite |
| 7,443,313 B2 | 10/2008 | Davis et al. |
| 7,444,401 B1 | 10/2008 | Keyghobad |
| 7,453,373 B2 | 11/2008 | Cumeralto et al. |
| 7,468,661 B2 | 12/2008 | Petite et al. |
| 7,478,108 B2 | 1/2009 | Townsend et al. |
| 7,480,501 B2 | 1/2009 | Petite |
| 7,497,957 B2 | 3/2009 | Frank |
| 7,523,016 B1 | 4/2009 | Surdulescu et al. |
| 7,526,539 B1 | 4/2009 | Hsu |
| 7,550,746 B2 | 6/2009 | Tokhtuev et al. |
| 7,650,425 B2 | 1/2010 | Davis |
| 7,697,492 B2 | 4/2010 | Petite |
| 7,739,378 B2 | 6/2010 | Petite |
| 7,752,309 B2 | 7/2010 | Keyghobad |
| 7,756,086 B2 | 7/2010 | Petite |
| 7,767,093 B2 | 8/2010 | Frank |
| 7,783,738 B2 | 8/2010 | Keyghobad |
| 7,792,946 B2 | 9/2010 | Keyghobad |
| 7,870,080 B2 | 1/2011 | Budike, Jr. |
| 7,920,983 B1 | 4/2011 | Peleg |
| 7,980,317 B1 * | 7/2011 | Preta | E03B 9/02 |
| | | | 169/60 |
| 8,082,945 B1 | 12/2011 | White et al. |
| 8,109,131 B2 | 2/2012 | Winter |
| 8,140,667 B2 | 3/2012 | Keyghobad et al. |
| 8,249,042 B2 | 8/2012 | Sparr et al. |
| 8,341,106 B1 | 12/2012 | Scolnicov et al. |
| 8,351,409 B2 | 1/2013 | Albert et al. |
| 8,360,720 B2 | 1/2013 | Schlabach et al. |
| 8,407,333 B2 | 3/2013 | Keyghobad |
| 8,423,637 B2 | 4/2013 | Vaswani et al. |
| 8,549,131 B2 | 10/2013 | Keyghobad et al. |
| 8,583,386 B2 | 11/2013 | Armon et al. |
| 8,615,374 B1 | 12/2013 | Discenzo |
| 8,823,509 B2 | 9/2014 | Hyland et al. |
| 9,053,519 B2 | 6/2015 | Scolnicov et al. |
| 9,104,189 B2 | 8/2015 | Berges Gonzalez et al. |
| 9,134,204 B2 * | 9/2015 | Mohajer | G01N 1/2035 |
| 9,202,362 B2 | 12/2015 | Hyland et al. |
| 9,441,988 B2 | 9/2016 | Armon et al. |
| 9,568,391 B2 | 2/2017 | Linford et al. |
| 9,568,392 B2 | 2/2017 | Peleg et al. |
| 9,583,386 B2 | 2/2017 | Kolics et al. |
| 9,588,094 B2 | 3/2017 | Wolfe |
| 9,604,858 B2 | 3/2017 | Kamen et al. |
| 9,749,792 B2 * | 8/2017 | Klicpera | G06Q 50/06 |
| 9,760,097 B2 | 9/2017 | Masias et al. |
| 9,777,457 B2 | 10/2017 | Mosley |
| 9,799,204 B2 | 10/2017 | Hyland et al. |
| 9,822,519 B2 | 11/2017 | Hall et al. |
| 9,863,425 B2 | 1/2018 | Kallesoe et al. |
| 9,934,670 B2 | 4/2018 | Hyland et al. |
| 9,952,605 B2 | 4/2018 | Griffin, Jr. et al. |
| 10,030,818 B2 | 7/2018 | Hoskins et al. |
| 10,180,414 B2 | 1/2019 | Clark et al. |
| 10,193,778 B2 | 1/2019 | Vaswani et al. |
| 10,203,315 B2 | 2/2019 | Clark et al. |
| 10,242,414 B2 | 3/2019 | Scolnicov et al. |
| 10,262,518 B2 | 4/2019 | Hyland et al. |
| 10,402,044 B2 | 9/2019 | Rose et al. |
| 10,410,501 B2 * | 9/2019 | Klicpera | G08B 21/18 |

(56) References Cited

U.S. PATENT DOCUMENTS

| | | |
|---|---|---|
| 10,489,038 B2 | 11/2019 | Klicpera |
| 10,508,966 B2 | 12/2019 | Tooms et al. |
| 10,564,802 B2 | 2/2020 | Rose et al. |
| 10,571,358 B2 | 2/2020 | Campan et al. |
| 10,837,858 B2 | 11/2020 | Seddiq et al. |
| 11,041,839 B2 | 6/2021 | Gifford et al. |
| 2001/0010032 A1 | 7/2001 | Ehlers et al. |
| 2001/0013488 A1 | 8/2001 | Fukunaga et al. |
| 2001/0024163 A1 | 9/2001 | Petite |
| 2001/0048030 A1 | 12/2001 | Sharood et al. |
| 2002/0002425 A1 | 1/2002 | Dossey et al. |
| 2002/0013679 A1 | 1/2002 | Petite |
| 2002/0019725 A1 | 2/2002 | Petite |
| 2002/0031101 A1 | 3/2002 | Petite |
| 2002/0043969 A1 | 4/2002 | Duncan |
| 2002/0062392 A1 | 5/2002 | Nishikawa et al. |
| 2002/0067717 A1 | 6/2002 | Raschke et al. |
| 2002/0073183 A1 | 6/2002 | Yoon et al. |
| 2002/0077777 A1 | 6/2002 | Wolfe et al. |
| 2002/0089802 A1 | 7/2002 | Beckwith |
| 2002/0105346 A1 | 8/2002 | Banks |
| 2002/0130069 A1 | 9/2002 | Moskoff |
| 2002/0130768 A1 | 9/2002 | Che et al. |
| 2002/0149487 A1 | 10/2002 | Haines |
| 2002/0154029 A1 | 10/2002 | Watters et al. |
| 2002/0169643 A1 | 11/2002 | Petite et al. |
| 2002/0190956 A1 | 12/2002 | Klein et al. |
| 2003/0009515 A1 | 1/2003 | Lee et al. |
| 2003/0018733 A1 | 1/2003 | Yoon et al. |
| 2003/0018776 A1 | 1/2003 | Yoon et al. |
| 2003/0036810 A1 | 2/2003 | Petite |
| 2003/0046377 A1 | 3/2003 | Daum et al. |
| 2003/0074109 A1 | 4/2003 | Jeong et al. |
| 2003/0093484 A1 | 5/2003 | Petite |
| 2003/0107485 A1 | 6/2003 | Zoratti |
| 2003/0174070 A1 | 9/2003 | Garrod et al. |
| 2004/0006513 A1 | 1/2004 | Wolfe |
| 2004/0010561 A1 | 1/2004 | Kim |
| 2004/0054747 A1 | 3/2004 | Breh |
| 2004/0064217 A1 | 4/2004 | Addink et al. |
| 2004/0129312 A1 | 7/2004 | Cuzzo et al. |
| 2004/0138840 A1 | 7/2004 | Wolfe |
| 2004/0139210 A1 | 7/2004 | Lee et al. |
| 2004/0154965 A1 | 8/2004 | Baum et al. |
| 2004/0158333 A1 | 8/2004 | Ha et al. |
| 2004/0159149 A1 | 8/2004 | Williams et al. |
| 2004/0183687 A1 | 9/2004 | Petite et al. |
| 2004/0199340 A1 | 10/2004 | Kersey et al. |
| 2004/0212510 A1 | 10/2004 | Aronstam |
| 2004/0237545 A1* | 12/2004 | Tanaka ................ F24F 3/06 62/99 |
| 2005/0007249 A1 | 1/2005 | Eryurek et al. |
| 2005/0009192 A1 | 1/2005 | Page |
| 2005/0084418 A1 | 4/2005 | Hill et al. |
| 2005/0096753 A1 | 5/2005 | Arling |
| 2005/0104747 A1 | 5/2005 | Silic et al. |
| 2005/0118704 A1 | 6/2005 | Malobabic |
| 2005/0120778 A1 | 6/2005 | Von Herzen et al. |
| 2005/0159823 A1 | 7/2005 | Hayes |
| 2005/0195768 A1 | 9/2005 | Petite et al. |
| 2005/0195775 A1 | 9/2005 | Petite et al. |
| 2005/0201379 A1 | 9/2005 | Zhang et al. |
| 2005/0201397 A1 | 9/2005 | Petite |
| 2005/0203647 A1 | 9/2005 | Landry et al. |
| 2005/0247114 A1 | 11/2005 | Kahn |
| 2005/0251366 A1 | 11/2005 | Kahn et al. |
| 2005/0251367 A1 | 11/2005 | Kahn et al. |
| 2005/0275527 A1 | 12/2005 | Kates |
| 2005/0279169 A1 | 12/2005 | Lander |
| 2006/0028355 A1 | 2/2006 | Pai et al. |
| 2006/0031040 A1 | 2/2006 | Wolfe |
| 2006/0041655 A1 | 2/2006 | Holloway et al. |
| 2006/0046664 A1 | 3/2006 | Paradiso et al. |
| 2006/0059977 A1 | 3/2006 | Kates |
| 2006/0098576 A1 | 5/2006 | Brownrigg et al. |
| 2006/0122736 A1 | 6/2006 | Alexanian |
| 2006/0158347 A1 | 7/2006 | Roche et al. |
| 2006/0174707 A1 | 8/2006 | Zhang |
| 2006/0181414 A1 | 8/2006 | Bandy et al. |
| 2006/0197345 A1 | 9/2006 | Kuroki et al. |
| 2006/0201550 A1 | 9/2006 | Blyth et al. |
| 2006/0218266 A1 | 9/2006 | Matsumoto et al. |
| 2006/0226970 A1 | 10/2006 | Saga et al. |
| 2006/0248961 A1 | 11/2006 | Shachar |
| 2006/0272830 A1 | 12/2006 | Fima |
| 2006/0273896 A1 | 12/2006 | Kates |
| 2007/0035315 A1 | 2/2007 | Hilleary |
| 2007/0050157 A1 | 3/2007 | Kahn et al. |
| 2007/0052540 A1 | 3/2007 | Hall et al. |
| 2007/0059986 A1 | 3/2007 | Rockwell |
| 2007/0063866 A1 | 3/2007 | Webb |
| 2007/0090059 A1 | 4/2007 | Plummer |
| 2007/0163965 A1 | 7/2007 | Wolfe |
| 2007/0219728 A1 | 9/2007 | Papageorgiou et al. |
| 2007/0293990 A1 | 12/2007 | Alexanian |
| 2007/0298779 A1 | 12/2007 | Wolman et al. |
| 2008/0030319 A1 | 2/2008 | Mckeena et al. |
| 2008/0095403 A1 | 4/2008 | Benhammou |
| 2008/0109090 A1 | 5/2008 | Esmaili et al. |
| 2008/0109175 A1 | 5/2008 | Michalak |
| 2008/0122641 A1 | 5/2008 | Amidi |
| 2008/0136191 A1 | 6/2008 | Baarman et al. |
| 2008/0149180 A1* | 6/2008 | Parris ................ E03B 7/072 137/1 |
| 2008/0155064 A1 | 6/2008 | Kosuge |
| 2008/0186898 A1 | 8/2008 | Petite |
| 2008/0195329 A1 | 8/2008 | Prince et al. |
| 2008/0289402 A1 | 11/2008 | Chowdhury |
| 2008/0291054 A1 | 11/2008 | Groft |
| 2009/0040057 A1 | 2/2009 | Keyghobad |
| 2009/0066524 A1 | 3/2009 | Yukawa et al. |
| 2009/0068947 A1 | 3/2009 | Petite |
| 2009/0084734 A1 | 4/2009 | Yencho |
| 2009/0099701 A1 | 4/2009 | Li et al. |
| 2009/0121860 A1 | 5/2009 | Kimmel et al. |
| 2009/0123340 A1 | 5/2009 | Knudsen et al. |
| 2009/0125241 A1 | 5/2009 | Frank |
| 2009/0157521 A1 | 6/2009 | Moren |
| 2009/0204265 A1* | 8/2009 | Hackett ............ G05B 19/4185 700/284 |
| 2009/0215424 A1 | 8/2009 | Petite |
| 2009/0243840 A1 | 10/2009 | Petite et al. |
| 2009/0260697 A1 | 10/2009 | Mevius et al. |
| 2009/0281677 A1 | 11/2009 | Botich et al. |
| 2009/0287838 A1 | 11/2009 | Keyghobad et al. |
| 2009/0287966 A1 | 11/2009 | Keyghobad |
| 2009/0301571 A1 | 12/2009 | Ruhs |
| 2009/0309755 A1 | 12/2009 | Williamson |
| 2009/0319853 A1 | 12/2009 | Keyghobad |
| 2010/0017465 A1 | 1/2010 | Brownrigg et al. |
| 2010/0039984 A1 | 2/2010 | Brownrigg |
| 2010/0085211 A1* | 4/2010 | Wang ................ G01F 1/10 340/870.02 |
| 2010/0105146 A1 | 4/2010 | Meeusen |
| 2010/0193430 A1 | 8/2010 | Whiteman |
| 2010/0194582 A1 | 8/2010 | Petite |
| 2010/0204924 A1 | 8/2010 | Wolfe et al. |
| 2010/0214120 A1 | 8/2010 | Means |
| 2010/0250054 A1 | 9/2010 | Petite |
| 2010/0265909 A1 | 10/2010 | Petite et al. |
| 2010/0312881 A1 | 12/2010 | Davis et al. |
| 2010/0313958 A1 | 12/2010 | Patel et al. |
| 2010/0332149 A1 | 12/2010 | Scholpp |
| 2011/0030482 A1 | 2/2011 | Meeusen et al. |
| 2011/0044276 A1 | 2/2011 | Albert et al. |
| 2011/0059462 A1 | 3/2011 | Lim et al. |
| 2011/0093123 A1 | 4/2011 | Alexanian |
| 2011/0111700 A1* | 5/2011 | Hackett ................ A01G 25/16 455/41.2 |
| 2011/0125412 A1 | 5/2011 | Salzer et al. |
| 2011/0132484 A1 | 6/2011 | Teach et al. |
| 2011/0178644 A1 | 7/2011 | Picton |
| 2011/0190947 A1 | 8/2011 | Savelle, Jr. et al. |
| 2011/0215945 A1 | 9/2011 | Peleg et al. |

(56) References Cited

U.S. PATENT DOCUMENTS

| | | |
|---|---|---|
| 2011/0233935 A1 | 9/2011 | Baarman et al. |
| 2011/0257788 A1 | 10/2011 | Wiemers et al. |
| 2011/0307203 A1 | 12/2011 | Higgins |
| 2011/0308638 A1 | 12/2011 | Hyland |
| 2012/0016823 A1 | 1/2012 | Paillet et al. |
| 2012/0025997 A1 | 2/2012 | Liu et al. |
| 2012/0038170 A1 | 2/2012 | Stuart et al. |
| 2012/0048386 A1 | 3/2012 | Clark |
| 2012/0106518 A1 | 5/2012 | Albert et al. |
| 2012/0116827 A1 | 5/2012 | Susumago |
| 2012/0118397 A1 | 5/2012 | Novotny et al. |
| 2012/0121386 A1* | 5/2012 | Dahlhaug ............ F03B 11/002 415/121.3 |
| 2012/0132445 A1 | 5/2012 | Mallon et al. |
| 2012/0191868 A1 | 7/2012 | Keyghobad |
| 2012/0206258 A1 | 8/2012 | Ramesh |
| 2012/0271686 A1 | 10/2012 | Silverman |
| 2012/0298208 A1 | 11/2012 | Taylor et al. |
| 2012/0298381 A1 | 11/2012 | Taylor |
| 2012/0311170 A1 | 12/2012 | Keyghobad et al. |
| 2013/0029683 A1 | 1/2013 | Kim et al. |
| 2013/0036800 A1 | 2/2013 | Mohajer |
| 2013/0041601 A1 | 2/2013 | Dintakurti et al. |
| 2013/0118239 A1 | 5/2013 | Forstmeier |
| 2013/0168327 A1 | 7/2013 | Clark |
| 2013/0170417 A1 | 7/2013 | Thomas et al. |
| 2013/0211797 A1 | 8/2013 | Scolnicov |
| 2013/0317659 A1 | 11/2013 | Thomas et al. |
| 2013/0332090 A1 | 12/2013 | Scolnicov et al. |
| 2013/0341934 A1 | 12/2013 | Kawanishi |
| 2014/0026644 A1 | 1/2014 | Patel et al. |
| 2014/0262998 A1 | 6/2014 | Wagner et al. |
| 2014/0224026 A1 | 8/2014 | Linford et al. |
| 2014/0278246 A1 | 9/2014 | Clark et al. |
| 2014/0340238 A1 | 11/2014 | Hyland |
| 2015/0198057 A1* | 7/2015 | Hanna ................ F01D 15/10 290/52 |
| 2015/0308627 A1 | 10/2015 | Hoskins |
| 2015/0327449 A1 | 11/2015 | Bartlett et al. |
| 2016/0049067 A1 | 2/2016 | Hyland |
| 2016/0163177 A1* | 6/2016 | Klicpera ............ E03B 7/071 137/59 |
| 2016/0356755 A1 | 12/2016 | Gifford |
| 2017/0059543 A1 | 3/2017 | Clark |
| 2017/0172078 A1* | 6/2017 | Gonzalez Hernandez ............ G05B 15/02 |
| 2017/0367578 A1 | 12/2017 | Melodia et al. |
| 2017/0370893 A1 | 12/2017 | West |
| 2018/0174424 A1 | 6/2018 | Hyland et al. |
| 2018/0372706 A1 | 12/2018 | Clark et al. |
| 2018/0372708 A1 | 12/2018 | Clark et al. |
| 2022/0018101 A1 | 1/2022 | Bowman et al. |

FOREIGN PATENT DOCUMENTS

| | | | |
|---|---|---|---|
| AU | 2014259545 | | 11/2015 |
| AU | 2015202223 | | 9/2016 |
| AU | 2014235054 | | 2/2018 |
| AU | 2018200410 | | 1/2019 |
| AU | 2018253559 | | 11/2020 |
| CA | 2634759 | | 12/2009 |
| CA | 2741843 | | 5/2018 |
| CA | 2772545 | | 12/2018 |
| CA | 2987661 | | 4/2021 |
| CA | 2900965 | | 9/2021 |
| CN | 1185838 | | 6/1998 |
| CN | 1458405 A * | | 11/2003 |
| CN | 2630512 Y * | | 8/2004 |
| CN | 101871834 | | 10/2010 |
| CN | 102095837 | | 6/2011 |
| CN | 204828756 | | 12/2015 |
| DE | 4016529 | | 11/1991 |
| DE | 4124154 A1 * | 1/1993 | ............ E03C 1/057 |
| DE | 202006017758 | | 2/2007 |
| EP | 1901253 | | 3/2008 |
| EP | 2433440 | | 7/2018 |
| EP | 2350992 | | 1/2019 |
| EP | 3422319 | | 1/2019 |
| EP | 3422320 | | 1/2019 |
| GB | 2305333 | | 4/1997 |
| GB | 2401406 A * | 11/2004 | ............ E02B 9/06 |
| GB | 2507184 | | 4/2014 |
| JP | 62-295674 | | 12/1987 |
| JP | 05-253316 | | 10/1993 |
| JP | 06-223279 | | 8/1994 |
| JP | 6300606 | | 10/1994 |
| JP | H0731989 | | 2/1995 |
| JP | 07-116285 | | 5/1995 |
| JP | 07231363 | | 8/1995 |
| JP | 2008128079 | | 5/1996 |
| JP | 11-046254 | | 2/1999 |
| JP | 2000285356 | | 10/2000 |
| JP | 2001200952 | | 7/2001 |
| JP | 2001254662 | | 9/2001 |
| JP | 2002014000 | | 1/2002 |
| JP | 2002352361 | | 12/2002 |
| JP | 2003172243 | | 6/2003 |
| JP | 2006285645 | | 10/2006 |
| JP | 2008198044 | | 8/2008 |
| JP | 2012507090 | | 3/2012 |
| JP | 2012527706 | | 11/2012 |
| JP | 2013200031 A * | | 10/2013 |
| KR | 20110092242 | | 8/2011 |
| WO | 9810299 | | 3/1998 |
| WO | 9810394 | | 3/1998 |
| WO | 03067021 | | 8/2003 |
| WO | 2008087911 | | 7/2008 |
| WO | 2009012254 | | 1/2009 |
| WO | WO-2009100476 A1 * | 8/2009 | ......... A01G 25/092 |
| WO | 2010051287 | | 5/2010 |
| WO | 2010099348 | | 9/2010 |
| WO | 2010135587 | | 11/2010 |
| WO | 2012069688 | | 5/2012 |
| WO | 2012099588 | | 7/2012 |
| WO | 2014151384 | | 9/2014 |
| WO | 2016197096 | | 12/2016 |

OTHER PUBLICATIONS

Machine Translation for CN2630512 (Year: 2004).*
Dictionary.com definition of "turbine" (Year: 2019).*
Machine Translation for CN1458405 (Year: 2003).*
Machine Translation for JP2013200031 (Year: 2013).*
Machine Translation for DE4124154 (Year: 1993).*
Hyland, Gregory E.; Corrected Notice of Allowance for U.S. Appl. No. 15/895,062, filed Feb. 13, 2018, dated Mar. 6, 2019, 7 pgs.
Hyland, Gregory E.; Issue Notification for U.S. Appl. No. 15/895,062, filed Feb. 13, 2018, dated Mar. 27, 2019, 1 pg.
Gifford, Paul; Final Office Action for U.S. Appl. No. 15/171,722, filed Jun. 2, 2016, dated Feb. 26, 2019, 18 pgs.
Gifford, Paul S.; European Search Report for serial No. 16804634.0, filed Jun. 6, 2016, dated Mar. 11, 2019, 19 pgs.
Whittle, et al; Article entitled: "WaterWise@SG: A Testbed for Continuous Monitoring of the Water Distribution System in Singapore", Water Distribution Analysis 2010, Dec. 21, 2011, 16, pgs.
Hyland, Gregory E.; International Search Report for serial No. PCT/US2009/062247, filed on Oct. 27, 2009, dated Dec. 18, 2009, 2 pgs.
Hyland, Gregory E.; Canadian Office Action for Serial No. 2,741,843, filed Oct. 27, 2009, dated Apr. 25, 2017, 7 pgs.
Hyland, Gregory E.; Canadian Office Action for serial No. 2,741,843, filed Oct. 27, 2009, dated Jul. 22, 2016, 5 pgs.
Hyland, Gregory E.; Canadian Office Action for serial No. 2,741,843, filed Oct. 27, 2009, dated Dec. 8, 2015, 5 pgs.
Hyland, Gregory; Mexico Office Action for serial No. MX/a/2011/004330, filed Apr. 25, 2011, dated Oct. 3, 2013, 6 pgs.
Hyland, Gregory; Mexico Office Action for serial No. MX/a/2011/004330, filed Apr. 25, 2011, dated Jul. 18, 2013, 6 pgs.
Hyland, Gregory;Mexico Office Action for serial No. MX/a/2011/004330, filed Apr. 25, 2011, dated Mar. 21, 2013, 7 pgs.

(56) References Cited

OTHER PUBLICATIONS

Hyland; European Examination Report for serial No. EP09824079.9, filed Oct. 27, 2009, dated Nov. 13, 2015; 6 pgs.
Hyland; European Search Report for serial No. EP09824079.9, filed Oct. 27, 2009, dated May 8, 2012; 38 pages.
Hyland, Gregory; Australian Patent Examination Report for serial No. 2009308949, filed Oct. 27, 2009, dated Nov. 12, 2013, 3 pgs.
Hyland, Gregory E.; Decision of Rejection for Japanese serial No. 2011-533427, filed Oct. 27, 2009, dated Sep. 16, 2014, 4 pgs.
Hyland, Gregory E.; Japanese Office Action for serial No. 2011-533427, filed Oct. 27, 2009, dated Feb. 4, 2014, 50 pgs.
Hyland, Gregory E.; Japanese Office Action for serial No. 2011-533427, filed Oct. 27, 2009, dated Apr. 30, 2013, 15 pgs.
Hyland, Gregory E.; Australian Examination Report for serial No. 2014259545, filed Oct. 27, 2009, dated Jun. 10, 2015; 2 pgs.
Hyland; International Preliminary Report on Patentability for serial No. PCT/US2010/035666, filed May 20, 2010, dated Nov. 22, 2011, 6 pgs.
Hyland, Gregory E.; Office Action for Canadian patent application No. 2,772,545, filed May 20, 2010, dated Jun. 22, 2017, 3 pgs.
Hyland; International Search Report and Written Opinion for serial No. PCT/US2010/035666, filed May 20, 2010, dated Jul. 16, 2010, 7 pgs.
Hyland, Gregory E.; Office Action for Canadian application No. 2,1/2,545, filed May 10, 2010, dated Jul. 27, 2016, 4 pgs.
Hyland, Gregory E.; Mexico Final Office Action for serial No. MX/A/2011/012383, filed May 20, 2010, dated Jan. 9, 2014, 9 pgs.
Hyland, Gregory E.; Mexico Office Action for serial No. MX/A/2011/012383, filed May 20, 2010, dated Sep. 3, 2013, 10 pgs.
Hyland, Gregory E.; Mexico Office Action for serial No. MX/A/2011/012383, filed May 20, 2010, dated May 9, 2013, 8 pgs.
Hyland, Gregory E.; Mexico Office Action for serial No. MX/A/2011/012383, filed May 20, 2010, dated Oct. 8, 2012, 3 pgs.
Hyland, Gregory E.; European Search Report for Serial No. EP10778423.3, filed Nov. 18, 2011, dated Apr. 10, 2017, 6 pgs.
Hyland, Gregory E.; European Search Report for serial No. EP2433440, filed Nov. 18, 2011, dated Nov. 28, 2012, 6 pgs.
Hyland, Gregory E.; Australian Patent Examination report for serial No. 2010249499, filed Nov. 17, 2011, dated Nov. 21, 2014, 5 pgs.
Hyland, Gregory E.; Australian Patent Examination report for serial No. 2010249499, filed Nov. 17, 2011, dated Mar. 16, 2014, 5 pgs.
Hyland, Gregory; Decision of Rejection for Japanese serial No. 2012-512048, filed May 20, 2010, dated Apr. 22, 2014, 10 pgs.
Hyland, Gregory; Japanese Office Action for serial No. 2012-512048, filed May 20, 2010, dated Oct. 22, 2013, 51 pgs.
Hyland, Gregory; Mexico Office Action for serial No. MX/a/2012/015236, filed Dec. 19, 2012, dated Dec. 3, 2013, received by foreign associate on Jan. 9, 2014, 4 pgs.
Hyland, Gregory; Mexico Office Action for serial No. MX/a/2012/015236, filed Dec. 19, 2012, dated Oct. 3, 2013, 8 pgs.
Hyland, Gregory; Mexico Office Action for serial No. MX/a/2012/015236, filed Dec. 19, 2012, dated Jun. 13, 2013, 4 pgs.
Hyland, Gregory E.; Australian Patent Examination report for serial No. 2015202223, filed May 20, 2010, dated Nov. 4, 2015, 4 pgs.
Hyland; U.S. Provisional Patent Application entitled: Water Supply Infrastructure Monitoring System and Method, having U.S. Appl. No. 61/108,770, filed Oct. 27, 2008, 11 pgs.
Hyland; U.S. Provisional Patent Application entitled: Water Supply Infrastructure Monitoring System and Method, having U.S. Appl. No. 61/180,600, filed May 22, 2009, 14 pgs.
Hyland; U.S. Provisional Patent Application entitled: Infrastructure Monitoring Devices, Systems, and Methods, having U.S. Appl. No. 61/355,468, filed Jun. 16, 2010.
Clark, Kenneth A.; Issue Notification for U.S. Appl. No. 14/209,257, filed Mar. 13, 2014, dated Sep. 26, 2018, 1 pg.
Clark, Kenneth A.; Notice of Allowance for U.S. Appl. No. 14/209,257, filed Mar. 13, 2014, dated Mar. 27, 2018, 26 pgs.
Clark, Kenneth A.; Non-Final Office Action for U.S. Appl. No. 14/209,257, filed Mar. 13, 2014, dated Oct. 16, 2017, 33 pgs.
Clark, Kenneth A.; Applicant-Initiated Interview Summary for U.S. Appl. No. 14/209,257, filed Mar. 13, 2014, dated Jul. 19, 2017, 7 pgs.
Clark, Kenneth A.; Final Office Action for U.S. Appl. No. 14/209,257, filed Mar. 13, 2014, dated Jun. 28, 2017, 41 pgs.
Clark, Kenneth A.; Non-final Office Action for U.S. Appl. No. 14/209,257, filed Mar. 13, 2014, dated Feb. 22, 2017, 95 pgs.
Clark, Kenneth A.; Restriction Requirement for U.S. Appl. No. 14/209,257, filed Mar. 13, 2014, dated Oct. 4, 2016, 7 pgs.
Clark, Kenneth A.; Notice of Allowance for U.S. Appl. No. 15/347,849, filed Nov. 10, 2016, dated Sep. 18, 2018, 20 pgs.
Clark, Kenneth A.; Final Office Action for U.S. Appl. No. 15/347,849, filed Nov. 10, 2016, dated Jun. 1, 2018, 29 pgs.
Wikipedia; Article entitled: "Water turbine", located at (https://en.wikipedia.org/wiki/Water_turbine), 11 pgs.
Clark, Kenneth A.; Non-Final Office Action for U.S. Appl. No. 15/347,849, filed Nov. 10, 2016, dated Nov. 3, 2017, 84 pgs.
Gifford, Paul; Non-Final Office Action for U.S. Appl. No. 15/171,722, filed Jun. 2, 2016, dated Aug. 29, 2018, 16 pgs.
Gifford, Paul; Final Office Action for U.S. Appl. No. 15/171,722, filed Jun. 2, 2016, dated Mar. 30, 2018, 15 pgs.
Gifford, Paul; Non-Final Office Action for U.S. Appl. No. 15/171,722, filed Jun. 2, 2016, dated Nov. 17, 2017, 90 pgs.
Gifford, Paul; Non-Final Office Action for U.S. Appl. No. 15/171,722, filed Jun. 2, 2016, dated Oct. 16, 2017, 76 pgs.
Hyland, Gregory E.; Applicant Initiated Interview Summary for U.S. Appl. No. 12/606,957, filed Oct. 27, 2009, dated Feb. 18, 2014, 4 pgs.
Hyland, Gregory E.; Final Office Action for U.S. Appl. No. 12/606,957, filed Oct. 27, 2009, dated Dec. 17, 2013, 54 pgs.
Hyland, Gregory E.; Final Office Action for U.S. Appl. No. 12/606,957, filed Oct. 27, 2009, dated Apr. 10, 2013, 80 pgs.
Hyland, Gregory E.; Final Office Action for U.S. Appl. No. 12/606,957, filed Oct. 27, 2009, dated Sep. 22, 2014, 49 pgs.
Hyland, Gregory E.; Issue Notification for U.S. Appl. No. 12/606,957, filed Oct. 27, 2009, dated Nov. 11, 2015, 1 pg.
Hyland, Gregory E.; Non-Final Office Action for U.S. Appl. No. 12/606,957, filed Oct. 27, 2009, dated Oct. 18, 2012; 44 pgs.
Hyland, Gregory E.; Non-Final Office Action for U.S. Appl. No. 12/606,957, filed Oct. 27, 2009, dated Apr. 8, 2014, 43 pgs.
Hyland, Gregory E.; Non-Final Office Action for U.S. Appl. No. 12/606,957, filed Oct. 27, 2009, dated Sep. 6, 2013; 53 pgs.
Hyland, Gregory E.; Non-Final Office Action for U.S. Appl. No. 12/606,957, filed Oct. 27, 2009, dated Apr. 16, 2015, 47 pgs.
Hyland, Gregory E.; Notice of Allowance for U.S. Appl. No. 12/606,957, filed Oct. 27, 2009, dated Jul. 27, 2015, 19 pgs.
Hyland, Gregory E.; Supplemental Notice of Allowability for U.S. Appl. No. 12/606,957, filed Oct. 27, 2009, dated Oct. 13, 2015, 4 pgs.
Hyland, Gregory E.; Final Office Action for U.S. Continuation U.S. Appl. No. 14/928,725, filed Oct. 30, 2015, dated Jul. 18, 2017, 51 pgs.
Hyland, Gregory E.; Issue Notification for U.S. Appl. No. 14/928,725, filed Oct. 30, 2015, dated Mar. 14, 2018, 1 pg.
Hyland, Gregory E.; Non-final Office Action for U.S. Continuation U.S. Appl. No. 14/928,725, filed Oct. 30, 2015, dated Jan. 25, 2017, 137 pgs.
Hyland, Gregory E.; Notice of Allowance for U.S. Appl. No. 14/928,725, filed Oct. 30, 2015, dated Nov. 30, 2017, 22 pgs.
Hyland, Gregory E.; Supplemental Notice of Allowance for U.S. Appl. No. 14/928,725, filed Oct. 30, 2015, dated Dec. 28, 2017, 6 pgs.
Hyland, Gregory E.; Supplemental Notice of Allowance for U.S. Appl. No. 14/928,725, filed Oct. 30, 2015, dated Feb. 27, 2018, 6 pgs.
Hyland, Gregory E.; Non-Final Office Action for U.S. Appl. No. 15/895,062, filed Feb. 13, 2018, dated Oct. 25, 2018, 72 pgs.
Hyland, Gregory E.; Final Office Action for U.S. Appl. No. 12/784,300, filed May 20, 2010, dated Feb. 11, 2014; 44 pgs.
Hyland, Gregory E.; Final Office Action for U.S. Appl. No. 12/784,300, filed May 20, 2010, dated May 29, 2013, 71 pgs.
Hyland, Gregory E.; Issue Notification for U.S. Appl. No. 12/784,300, filed May 20, 2010, dated Aug. 13, 2014. 1 pg.

(56) References Cited

OTHER PUBLICATIONS

Hyland, Gregory E.; Non-Final Office Action for U.S. Appl. No. 12/784,300, filed May 20, 2010, dated Sep. 10, 2012, 35 pgs.
Hyland, Gregory E.; Non-Final Office Action for U.S. Appl. No. 12/784,300, filed May 20, 2010, dated Sep. 24, 2013; 37 pgs.
Hyland, Gregory E.; Notice of Allowance for U.S. Appl. No. 12/784,300, filed May 20, 2010, dated Apr. 23, 2014, 20 pgs.
Hyland, Gregory E.; Supplemental Notice of Allowability for U.S. Appl. No. 12/784,300, filed May 20, 2010, dated Aug. 1, 2014, 4 pgs.
Hyland, Gregory E.; Final Office Action for U.S. Appl. No. 14/450,452, filed Aug. 4, 2014, dated Aug. 23, 2016, 41 pgs.
Hyland, Gregory E.; Non-Final Office Action for U.S. Appl. No. 14/450,452, filed Aug. 4, 2014, dated Feb. 17, 2016, 98 pgs.
Hyland, Gregory E.; Non-final Office Action for U.S. Appl. No. 14/450,452, filed Aug. 4, 2014, dated Feb. 2, 2017, 40 pgs.
Hyland, Gregory E.; Notice of Allowability for U.S. Appl. No. 14/450,452, filed Aug. 4, 2014, dated Jul. 18, 2017, 6 pgs.
Hyland, Gregory E.; Notice of Allowance for U.S. Appl. No. 14/450,452, filed Aug. 4, 2014, dated Jun. 15, 2017, 17 pgs.
Hyland, Gregory; Corrected Notice of Allowability for U.S. Appl. No. 14/450,452, filed Aug. 4, 2014, dated Sep. 26, 2017, 4 pgs.
Hyland, Gregory; Issue Notification for U.S. Appl. No. 14/450,452, filed Aug. 4, 2014, dated Oct. 4, 2017, 1 pg.
Keyghobad, Seyamak; Issue Notification for U.S. Appl. No. 10/298,300, filed Nov. 18, 2002, dated Oct. 8, 2008; 1 pg.
Keyghobad, Seyamak; Requirement for Restriction/ Election for U.S. Appl. No. 10/298,300; filed Nov. 18, 2002; dated Feb. 9, 2006; 11 pages.
Keyghobad, Seyamak; Issue Notification for U.S. Appl. No. 12/243,452, filed Oct. 1, 2008 dated Jun. 16, 2010; 1 pg.
Keyghobad, Seyamak; Issue Notification for U.S. Appl. No. 12/490,867, filed Jun. 24, 2009, dated Feb. 29, 2012; 1 pg.
Keyghobad, Seyamak; Non Final Rejection for U.S. Appl. No. 12/490,867, filed Jun. 24, 2009, dated Mar. 21, 2011; 9 pgs.
Keyghobad, Seyamak; Non Final Rejection for U.S. Appl. No. 12/490,867, filed Jun. 24, 2009, dated Oct. 4, 2010; 13 pgs.
Keyghobad, Seyamak; Notice of Allowance for U.S. Appl. No. 12/490,867, filed Jun. 24, 2006, dated Sep. 7, 2011; 6 pgs.
Keyghobad, Seyamak; Notice of Allowance for U.S. Appl. No. 12/490,867, filed Jun. 24, 2009, dated Nov. 2, 2011; 17 pgs.
Keyghobad, Seyamak; Issue Notification for U.S. Appl. No. 12/490,925, filed Jun. 24, 2009; dated Aug. 18, 2010; 1 pg.
Keyghobad, Seyamak; Non-final office action for U.S. Appl. No. 12/490,925, filed Jun. 24, 2009; dated Dec. 23, 2009; 17 pgs.
Keyghobad, Seyamak; Notice of Allowance for U.S. Appl. No. 12/490,925, filed Jun. 24, 2009, dated Aug. 2, 2010, 8 pgs.
Keyghobad, Seyamak; Issue Notification for U.S. Appl. No. 12/490,957, filed Jun. 24, 2009; dated Aug. 4, 2010; 1 pg.
Keyghobad, Seyamak; Issue Notification for U.S. Appl. No. 13/372,408, filed Feb. 13, 2012, dated Mar. 6, 2013, 1 pg.
Keyghobad, Seyamak; Non-final Office Action for U.S. Appl. No. 13/372,408, filed Feb. 23, 2012; dated May 25, 2012; 17 pgs.
Keyghobad, Seyamak; Notice of Allowance for U.S. Appl. No. 13/372,408, filed Feb. 13, 2012, dated Jul. 27, 2012; 11 pgs.
Keyghobad, Seyamak; Notice of Allowance for U.S. Appl. No. 13/372,408, filed Feb. 13, 2012, dated Nov. 1, 2012; 18 pgs.
Keyghobad, Seyamak; Supplemental Notice of Allowance for U.S. Appl. No. 13/372,408, filed Feb. 13, 2012; dated Aug. 2, 2012; 7 pgs.
Keyghobad, Seyamak, Issue Notification for U.S. Appl. No. 13/590,954, filed Aug. 21, 2012, dated Sep. 11, 2013, 1 pg.
Hyland, Gregory E.; Notice of Allowance for U.S. Appl. No. 15/895,062, filed Feb. 13, 2018, dated Dec. 26, 2018, 11 pgs.
Hyland, Gregory E.; Office Action for Canadian patent application No. 2,997,878, filed Oct. 27, 2009, dated Dec. 10, 2018, 4 pgs.
Icelandic Building Research Institute, et al.; "Monitoring corrosion in district heating systems", Nordic Innovation, Project No. 00071, Final Report, pp. 1-254, May 2004 (May 2004).

Hyland, Gregory E.; Extended European Search Report for serial No. 18184468.9, filed May 20, 2010, dated Dec. 3, 2018, 9 pgs.
Hyland, Gregory E.; Extended European Search Report for serial No. 18184481.2, filed May 20, 2010, dated Dec. 3, 2018, 9 pgs.
Clark, Kenneth A.; Issue Notification for U.S. Appl. No. 14/209,257, filed Mar. 13, 2014, dated Dec. 22, 2018, 1 pg.
Clark, Kenneth A.; Issue Notification for U.S. Appl. No. 15/347,849, filed Nov. 10, 2016, dated Jan. 23, 2019, 1 pg.
Vonroll Hydro—Hydrojournal, pp. 1-16, May 2008.
English Translation: Vonroll Hydro—Hyrdojournal, Technology with a Future for Shut-off Systems—p. 4, VonRoll Hydro (shop) GmbH—New Concepts for Apprentice Training—p. 12, May 2008.
Von Roll Hydro—Hydrojournal, pp. 1-16, Nov. 2008.
English Translation: Von Roll Hydro—Hyrdojournal,VonRoll Hydroalert—Provides a Warning in the Event of Any Tampering with the Water Supply, p. 3, Nov. 2008.
Keyghobad, Seyamak; Examiner Interview Summary Record for U.S. Appl. No. 10/298,300; filed Nov. 18, 2002; dated Feb. 5, 2008; 2 pages.
Keyghobad, Seyamak; Non-Final Rejection for U.S. Appl. No. 10/298,300; filed Nov. 18, 2002; dated Oct. 26, 2007; 35 pages.
Keyghobad, Seyamak; Requirement for Restriction/ Election for U.S. Appl. No. 10/298,300; filed Nov. 18, 2002; dated Feb. 27, 2006; 17 pages.
Keyghobad, Seyamak; Certificate of Correction for U.S. Appl. No. 10/298,300; filed Nov. 18, 2002; dated Mar. 31, 2009; 1 page.
Keyghobad, Seyamak; Notice of Allowance for U.S. Appl. No. 10/298,300; filed Nov. 18, 2002; dated Jul. 14, 2008; 4 pages.
Keyghobad, Seyamak; Non-Final Rejection or U.S. Appl. No. 10/298,300; filed Nov. 18, 2002; dated Jun. 6, 2007; 32 pages.
Keyghobad, Seyamak; Non-Final Rejection for U.S. Appl. No. 10/298,300; filed Nov. 18, 2002; dated May 18, 2006; 13 pages.
Keyghobad, Seyamak; Notice of Allowance for U.S. Appl. No. 12/243,452, filed Oct. 1, 2008; dated Mar. 22, 2010; 7 pages.
Keyghobad, Seyamak; Examiner Interview Summary Record for U.S. Appl. No. 12/243,452, filed Oct. 1, 2008; dated Dec. 7, 2009; 3 pages.
Keyghobad, Seyamak; Non-Final Rejection for U.S. Appl. No. 12/243,452, filed Oct. 1, 2008; dated Sep. 14, 2009; 12 pages.
Keyghobad,Seyamak; Non-Final Rejection for U.S. Appl. No. 12/243,452, filed Oct. 1, 2008; dated May 1, 2009; 5 pages.
Hyland; International Preliminary Report on Patentability for serial No. PCT/US2009/062247, filed Oct. 27, 2009, dated May 3, 2011, 7 pgs.
Keyghobad, Seyamak; Notice of Allowance for U.S. Appl. No. 12/490,925, filed Jun. 24, 2009; dated Jul. 19, 2010; 8 pages.
Keyghobad, Seyamak; Notice of Allowance for U.S. Appl. No. 12/490,925, filed Jun. 24, 2009; dated Jun. 28, 2010; 10 pgs.
Keyghobad, Seyamak; Notice of Allowance for U.S. Appl. No. 12/490,957, filed Jun. 24, 2009; dated Jun. 24, 2010; 10 pgs.
Keyghobad,Seyamak; Non-Final Rejection for U.S. Appl. No. 12/490,957, filed Jun. 24, 2009; dated Dec. 23, 2009; 17 pgs.
Radix Corporation; "Automatic Meter Reading", 2 pgs.
Trace; "Pit Water-Meter Transponder"; User Guide; Jan. 2003 16 pgs.
Keyghobad, Seyamak; Non-Final Office Action for U.S. Appl. No. 13/590,954, filed Aug. 21, 2012, dated Dec. 13, 2012; 39 pgs.
ANSI; "Protocol Specification for ANSI Type 2 Optical Port", American National Standard, ANSI C.12.18-2006,11 pgs.
Federal Communications Commission; "Understanding the FCC Regulations for Low-Power, Non-Licensed Transmitters", Office of Engineering and Technology; Oct. 1993; 34 pgs.
Semtech; "TN1200.4, Calculating Radiated Power and Field Strength for Conducted Power Measurements", Semtech Corporation, Camarillo, CA, 2007, 9 pgs.
RFM; "HX 2000 Datasheet: 916.5 MHz: Hybrid Transmitter", RF Monolithics, Inc., Dallas, TX, USA, 1998; 2 pgs.
General Electric; "GEH-5081 kV Meter Product Manual", Nov. 1997, 137 pgs.
General Electric; "kV RSX-RS232/RS485 Communications Options: Instructions Manual"; Mar. 1999, 33 pgs.

(56) References Cited

OTHER PUBLICATIONS

Orfield; "Badger® ORION® System Helps Lemmon, South Dakota Reduce Read Time, Billing Cycles", Badger Connect Publication, 2004, 2 pgs.
AMCO; "Pit Water-Meter Transponder (PWT)"; AMCO Automated Systems, LLC; PDB-14611; Sep. 2002; 2 pgs.
AMCO; "Short-Range Programmer (SRP) VRT"; AMCO Automated Systems, LLC; PDB-14555.1; Sep. 2002; 2 pgs.
AMCO; Remote Water-Meter Transponder (RWT); AMCO Automated Systems, LLC; PDB-14610; Sep. 2002; 2 pgs.
Article entitled: "Remote Meter Reading", http://www.meter.co.uk/RMR.html; accessed on Jul. 30, 2012, 2 pgs.
Article entitled: "Datamatic, Badger Connect for AMR Solutions", http://www.datamatic.com/badger_partnership.html; accessed on Jul. 27, 2012, 1 pg.
Article entitled: "OET Exhibits List", https://apps.fcc.gov/oetcf/eas/reports/ViewExhibitReport.cfm?mode=Exhibits&RequestTimeout=500&calledFromFrame=N&application_id=194044&fcc_id=; Feb. 20, 2001, 2 pgs.
Patterson, Tim; Request for Ex Parte Reexamination under U.S. Appl. No. 90/012,468, filed Sep. 6, 2012; 52 pgs.
Patterson, Tim; Request for Ex Parte Reexamination under U.S. Appl. No. 90/012,449, filed Aug. 23, 2012; 51 pgs.
"Young et al. "Real-Time Intranet-Controlled Virtual Instrument Multiple-Circuit Power Monitoring," IEEE Transactions an Instrumentation and Measurement, Jun. 2000. vol. 49, No. 3, p. 570. [Accessed Dec. 29, 2011]http://ieeexplore.ieee.org/xpls/abs_all.jsp?".
"De Almeida et al. "Advanced Monitoring Technologies for the Evaluation of Demand-Side Management Programs," EEE Transactions on Power Systems, Aug. 1994. vol. 9, No. 3. [Accessed Dec. 29, 2011]http://ieeexplore.ieee.org/xpls/abs_all.jsp?arnumber=336086".
"Dolezilek. "Microprocessor Based Relay Information Improves the Power System," Rural Electric Power Conference, May 1999. p. B5/1-B5/9. [Accessed Dec. 29, 2011]http://ieeexplore.ieee.org/xpls/abs_all.jsp?arnumber=768685".
Gehami et al. "Electronic Control System I Salient Feature in Substation," Transmission & Distrubition, Mar. 1991. vol. 43, No. 3, p. 48. [Accessed Dec. 29, 2011—ProQuest].
Horlent. "New Metering and Reading Techniques Based on a Modular Design Concept," 10th International Conference on Electricity Distribution, May 1989. vol. 5, p. 455-459. [Accessed Dec. 29, 2011—IEEExplore].
""In Brief," Land Mobile Radio News, Jan. 16, 1998. vol. 52, No. 3, p. 1. [Accessed Dec. 29, 2011—ProQuest] http://proquest.umi.com/pqdweb?did=25435781&sid=1&Fmt=3&clientId=31810&RQT=309&VName%20=PQD".
""Landis & Gyr Utilities: Service Partnership Helps Utilities Use Available Resources More Effectively," www.landisgyr.com/utilities/e/fr_press1_e.htm (archived Feb. 6, 1998) http://web.archive.org/web/19980206060801/http://www.landisgyr.com/utilities".
Tamarkin. "Automated Meter Reading", Sep.-Oct. 1992, vol. 50, No. 5/ [Accessed Dec. 29, 2011] http://www.usclcorp.com/news/Automatic_Power_reading.pdf.
Keyghobad, Seyamak; Notice of Allowance for U.S. Appl. No. 13/590,954, filed Aug. 21, 2012, dated Jul. 9, 2013, 21 pgs.
Keyghobad, Seyamak; Notice of Allowance for U.S. Appl. No. 13/590,954, filed Aug. 21, 2012, dated Mar. 21, 2013, 22 pgs.
Clark, Kenneth A.; Non-Final Office Action for U.S. Appl. No. 16/118,914, filed Aug. 31, 2018, dated Sep. 9, 2019, 107 pgs.
Whittle, et al.; Article entitled: "WaterWise@SG: A Testbed for Continuous Monitoring of the Water Distribution System in Singapore", Water Distribution Analysis 2010—WDSA2010, Tucson, AZ, USA, Sep. 12-15, 2010; 16 pgs.
Gifford, Paul; Notification of Non-Compliant Appeal Brief for U.S. Appl. No. 15/171,722, filed Jun. 2, 2016, dated Jun. 25, 2019, 2 pgs.
Clark, Kenneth A.; Examination Report for Australian patent application No. 2018253559, filed Mar. 13, 2014, dated Jul. 8, 2019, 3 pgs.

Gifford, Paul S.; European Search Report for serial No. 16804634.0, filed Jun. 6, 2016, dated Jul. 25, 2019, 21 pgs.
Shafiee, et al.; Article entitled: "Integrating Evolutionary Computation and Sociotechnical Simulation for Flushing Contaminated Water Distribution Systems", Genetic and Evolutionary Computation, ACM, Jul. 1, 2012, pp. 315-322 (8 pgs).
Clark, Kenneth A.; International Preliminary Report on Patentability for PCT/US2014/025617, filed Mar. 13, 2014, dated Sep. 24, 2015, 12 pgs.
Clark, Kenneth A.; International Search Report and Written Opinion for serial No. PCT/US2014/025617, filed Mar. 13, 2014, dated Aug. 27, 2014, 48 pgs.
Huang, et al.; "The Mahalanobis-Taguchi system—Neural network algorithm for data mining in dynamic environments". Extern Systems with Appklications (online), 2009 [retrieved on Aug. 13, 2014], vol. 36, pp. 5475-5480.
Clark, Kenneth A.; Extended European Search Report for serial No. 14771115.4, filed Mar. 13, 2014, dated Sep. 14, 2016, 8 pgs.
Stoianov, et al.; Article entitled: "Sensor Networks for Monitoring Water Supply and Sewer Systems: Lessons from Boston", Water Distribution Systems Analysis Symposium 2006; , Aug. 27-30, 2006, 17 pgs.
Perelman, et al.; Article entitled: "Event Detection in Water Distribution Systems from Multivariate Water Quality Time Series", Environmental Science & Technology, vol. 46, No. 15, Aug. 7, 2012, 8 pgs.
Palau, et al.; Article entitled: "Using . . .", Water Science and Technology: Water Supply, vol. 4, No. 3, Jun. 30, 2004, 12 pgs.
Clark, Kenneth A.; Office Action for Mexico Application No. MX/a/2015/011793, filed Mar. 13, 2014, dated Jun. 20, 2017, 8 pgs.
Clark, Kenneth A.; Office Action for Mexico Application No. MX/a/2015/011793, filed Mar. 13, 2014, dated Feb. 20, 2017, 7 pgs.
Clark, Kenneth A.; Office Action for Australian Application No. 2014235054, filed Mar. 13, 2014, dated Jun. 2, 2017, 3 pgs.
Clark, Kenneth A.; Examination Report for Australian application No. 2018200410, filed Mar. 13, 2014, dated Jun. 28, 2018, 4 pgs.
Gifford, Paul; Notification Concerning International Preliminary Report on Patentability for PCT Application No. PCT/US16/36007, filed Jun. 6, 2016, dated Dec. 14, 2017, 9 pgs.
Gifford, Paul; International Search Report and Written Opinion for PCT Application No. PCT/US16/36007, filed Jun. 6, 2016, dated Oct. 6, 2016, 12 pgs.
Clark, Kenneth A.; U.S. Provisional Patent Application entitled: Systems for Measuring Properties of Water in a Water Distribution System , U.S. Appl. No. 61/794,616, filed Mar. 15, 2013; 49 pgs.
Gifford, Paul; U.S. Provisional Patent Application entitled: Distribution System Monitoring having U.S. Appl. No. 62/171,897, filed Jun. 5, 2015, 42 pgs.
Gifford, Paul S.; Office Action for Canadian patent application No. 2,987,661, filed Jun. 6, 2016, dated Nov. 26, 2019, 4 pgs.
Clark, Kenneth A.; Final Office Action for U.S. Appl. No. 16/118,914, filed Aug. 31, 2018, dated Mar. 23, 2020, 52 pgs.
Clark, Kenneth A.; Examination Report for Australian patent application No. 2018253559, filed Mar. 13, 2014, dated Jan. 17, 2020, 3 pgs.
Hyland, Gregory E.; Office Action for Canadian patent application No. 2,997,878, filed Oct. 27, 2009, dated Sep. 27, 2019, 5 pgs.
Hyland, Gregory E.; Extended European Search Report for serial No. 18214263.8, filed Oct. 27, 2009, dated Sep. 2, 2019, 11 pgs.
Clark, Kenneth A.; Non-Final Office Action for U.S. Appl. No. 16/118,907, filed Aug. 31, 2018, dated Oct. 11, 2019, 104 pgs.
Hyland, Gregory E.; Office Action for Canadian patent application No. 2,997,878, filed Oct. 27, 2009, dated Nov. 25, 2020, 7 pgs.
Clark, Kenneth A.; Office Action for Canadian application No. 2,900,965, filed Mar. 13, 2014, dated Oct. 27, 2020, 4 pgs.
Hyland, Gregory E.; Office Action for Canadian patent application No. 2,997,878, filed Oct. 27, 2009, dated Apr. 2, 2020, 7 pgs.
Clark, Kenneth A.; Final Office action for U.S. Appl. No. 16/118,907, filed Aug. 31, 2018, dated Apr. 16, 2020, 35 pgs.
Clark, Kenneth A.; Office Action for Canadian application No. 2,900,965, filed Mar. 13, 2014, dated Jan. 20, 2020, 5 pgs.
Clark, Kenneth A.; Office Action for Canadian application No. 2,900,965, filed Mar. 13, 2014, dated Jun. 12, 2020, 4 pgs.

(56) References Cited

OTHER PUBLICATIONS

Clark, Kenneth A.; Examination Report for Australian patent application No. 2018253559, filed Mar. 13, 2014, dated Apr. 28, 2020, 3 pgs.
Gifford, Paul S.; Office Action for Canadian patent application No. 2,987,661, filed Jun. 6, 2016, dated Apr. 21, 2020, 3 pgs.
Gifford, Paul; Non-Final Office Action for U.S. Appl. No. 15/171,722, filed Jun. 2, 2016, dated Oct. 5, 2020, 39 pgs.
Gifford, Paul S.; Office Action for Canadian patent application No. 2,987,661, filed Jun. 6, 2016, dated Aug. 17, 2020, 3 pgs.
Hyland, Gregory E.; Office Action for Canadian patent application No. 2,997,878, filed Oct. 27, 2009, dated Jul. 16, 2020, 7 pgs.
Hyland, Gregory E.; Office Action for European serial No. 18214263.8, filed Oct. 27, 2009, dated Jul. 14, 2020, 5 pgs.
Clark, Kenneth A.; Office Action for European serial No. 14771115.4, filed Mar. 13, 2014, dated Sep. 9, 2020, 4 pgs.
Hunaidi, et al., "A new System for locating leaks in urban water distribution pipes", International Journal of Management of Environmental Quality, Jan. 31, 2006, pp. 450-466, Retrieved from the internet: <http://web.mit.edu/parmstr/Public/NRCan/nrcc48357.pdf>, 19 pgs.
Clark, Kenneth A.; Non-Final Office Action for U.S. Appl. No. 16/118,914, filed Aug. 31, 2018, dated Mar. 4, 2021, 55 pgs.
Gifford, Paul; Notice of Allowance for U.S. Appl. No. 15/171,722, filed Jun. 2, 2016, dated Feb. 10, 2021, 26 pgs.
Environmental Protection Agency; Article entitled: "Technologies and Techniques for Early Warning Systems to Monitor and Evaluate Drinking Water Quality: A Stage of the Art Review", located at <https://cfpub.epa.gov/si/si_public_record_report.cfm?Lab=NHSRC&address=nhsrc/&dirE ntryld=144729>, Oct. 2005, 3 pgs.
Honeywell; Article entitled: "Corrosion Solutions for Multiphase Oil & Gas Production", located at <http://cindtechs.ca/unleashd/catalog/analytical/Honeywell-CET5000/pi_sn_Multiphase_09.pdf>, Aug. 2006, 2 pgs.
Hyland, Gregory E.; Office Action for Canadian patent application No. 2,997,878, filed Oct. 27, 2009, dated May 25, 2021, 13 pgs.
Perkins; Article entitled: "New Developments in Microcor Technology", located at <https://www.cosasco.com/resources/technical-library/technical-papers>, las modified Nov. 27, 2007, 17 pgs.
Hyland, Gregory E.; Office Action for European application No. 18214263.8, filed Oct. 27, 2009, dated Mar. 1, 2021, 7 pgs.
Gifford, Paul; Corrected Notice of Allowance for U.S. Appl. No. 15/171,722, filed Jun. 2, 2016, dated May 14, 2021, 7 pgs.
Gifford, Paul; Corrected Notice of Allowance for U.S. Appl. No. 15/171,722, filed Jun. 2, 2016, dated Apr. 16, 2021, 5 pgs.
Hyland, Gregory E.; Office Action for European patent application No. 18184481.2, filed May 20, 2010, dated May 10, 2021 (received by European counsel for Applicant on Oct. 16, 2021), 7 pgs.
Clark, Kenneth A.; Final Office Action for U.S. Appl. No. 16/118,914, filed Aug. 31, 2018, dated Sep. 3, 2021, 22 pgs.
Clark, Kenneth A.; Examination Report for Australian patent application No. 2020257082, filed Mar. 13, 2014, dated Oct. 26, 2021, 3pgs.
Hyland, Gregory E.; Office Action for European patent application No. 18184468.9, filed May 20, 2010, dated Jul. 5, 2021 (received by European counsel for Applicant on Aug. 20, 2021), 6 pgs.
Clark, Kenneth A.; Notice of Allowance for U.S. Appl. No. 16/118,914, filed Aug. 31, 2018, dated Nov. 9, 2021, 10 pgs.
Hyland, Gregory E.; Office Action for Canadian patent application No. 2,997,878, filed Oct. 27, 2009, dated Oct. 29, 2021, 10 pgs.
Clark, Kenneth A.; Office Action for European patent application No. 14771115.4, filed Mar. 13, 2014, dated Dec. 15, 2021, 5 pgs.
Lambrou, et al.; Article entitled: "A Low-Cost Sensor Network for Real-Time Monitoring and Contamination Detection in Drinking Water Distribution Systems", IEEE Sensors Journal, vol. 14, No. 8, Aug. 2014, 9 pgs.
Gifford, Paul S.; Office Action for European patent application No. 16804634.0, filed Jun. 6, 2016, dated Dec. 9, 2021, 7 pgs.
Clark, Kenneth A.; Examination Report for Australian patent application No. 2020257082, filed Mar. 13, 2014, dated Jan. 11, 2022, 8 pgs.
Onset Computer Corporation; Article entitled: HOBOLINK Printable Help; located at <https://www.onsetcomp.com/files/manual_pdfs/11969_E_MAN_HL_WH.pdf>, retrieved Jan. 11, 2022, published 2008, 112 pgs.
SensorsONE Measurement Instrumentation Products; Article entitled: "Triton Data Logger Series", retrieved from internet Jan. 11, 2022, <https://www.sensorsone.com/wp-content/uploads/2013/02/Triton-Series.pdf>, published Feb. 28, 2013, 5 pgs.

* cited by examiner

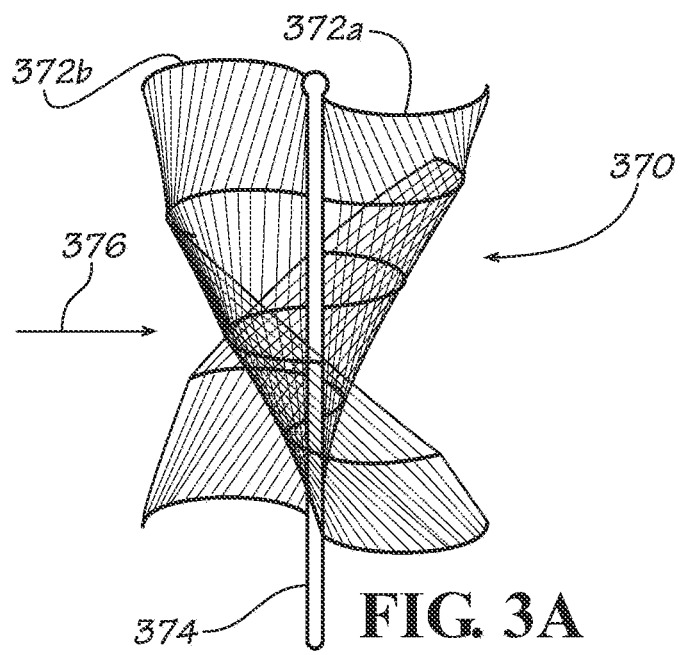
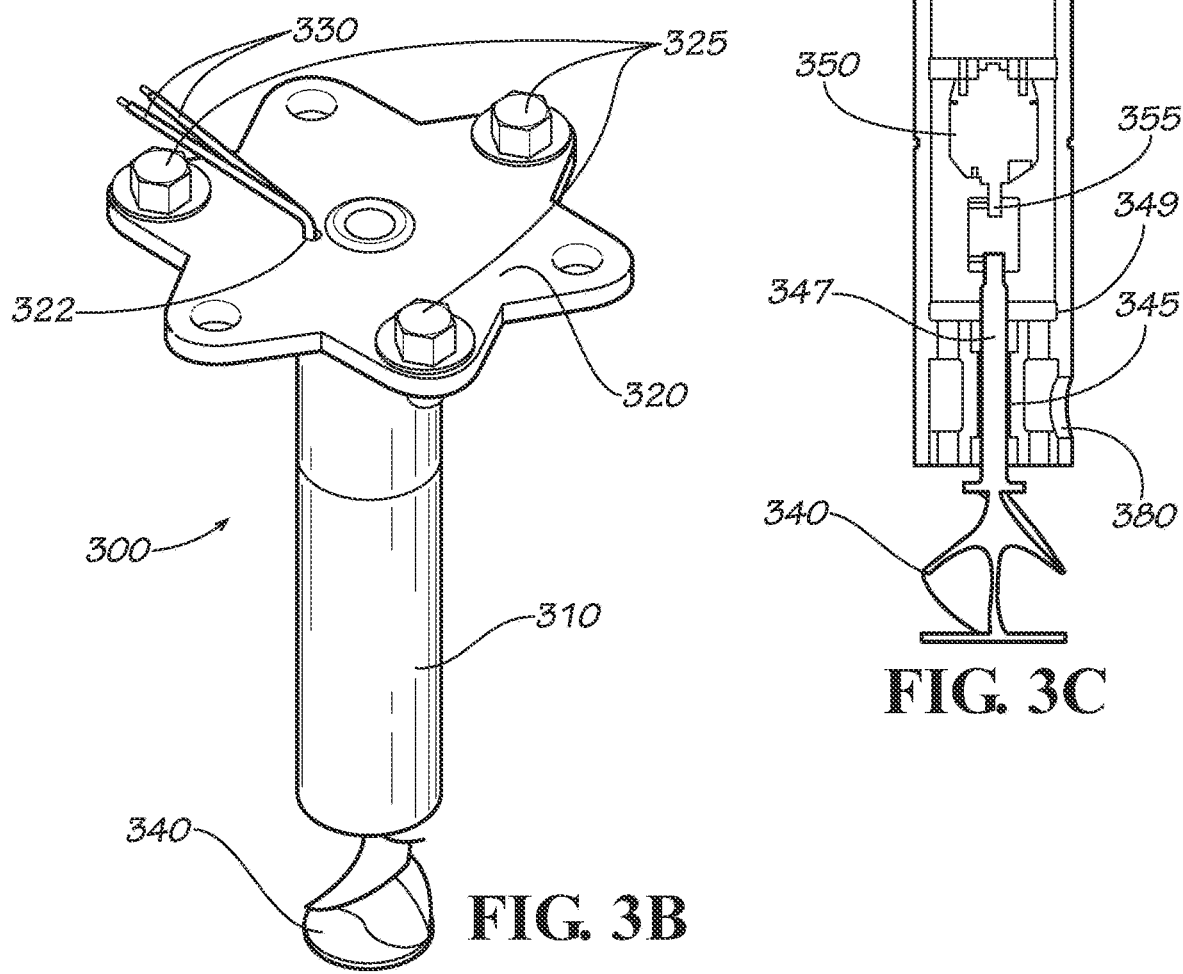

SYSTEMS FOR MEASURING PROPERTIES OF WATER IN A WATER DISTRIBUTION SYSTEM

REFERENCE TO RELATED APPLICATIONS

This application is a divisional of U.S. patent application Ser. No. 14/209,257, filed on Mar. 13, 2014, which claims the benefit of U.S. Provisional Application No. 61/794,616, filed Mar. 15, 2013, both of which are hereby specifically incorporated by reference herein in their entireties.

TECHNICAL FIELD

The present disclosure generally relates to water distribution systems, and more particularly relates to measuring properties of water in a water distribution system and managing the measurement data.

BACKGROUND

Water utility companies provide water to customers through a network of water pipes. This network of pipes can be referred to as a water distribution system.

SUMMARY

The present disclosure provides systems and methods for measuring properties of water in a water distribution system. In various embodiments, a non-transitory web application is stored on a computer-readable medium, wherein the web application comprises web site logic, browser interface logic, an application programming interface, and a database. The web site logic is configured to maintain a web site having at least one web page. The browser interface logic is configured to enable a remote device to access the at least one web page. The application programming interface is configured to interface with the remote device to enable the remote device to access the web application. The database is configured to store water data related to a plurality of water measurements. The web site logic is further configured to receive a data request from the remote device, search the database in response to the data request to obtain at least one water measurement, and send the at least one water measurement to the remote device.

In addition, according to various embodiments of the present disclosure, an analysis system is provided. The analysis system comprises a plurality of water sensors connected at various points to a water distribution system, each of the plurality of water sensors configured to measure a property of water. The analysis system also includes a computer server configured to communicate with the plurality of water sensors via a network and receive water measurement data from the plurality of water sensors. The computer server comprises a processor, a database configured to store the water measurement data, and a system health monitoring module configured to evaluate the health of the water distribution system to obtain health data. The analysis system further includes at least one client device configured to communicate with the computer server via the network and receive the health data from the computer server.

In addition, in various embodiments, a water sensing assembly is disclosed. The water sensing assembly comprises a valve box securely mountable on an underground water pipe. The water sensing assembly also includes a sensor mounted inside the valve box, wherein the sensor is configured to sense a property of water within the underground water pipe. Also included is a top section connected to the valve box. An electrical communication device is mounted at a top portion of the adjustable top section such that the electrical communication device is positioned at or near the surface of the ground.

A service saddle is also provided, wherein the service saddle comprises a lower channel alignable with a bore in a water pipe. The service saddle also includes a main port having an interior volume opened to the lower channel and a secondary port having an interior volume opened to the lower channel. The service saddle further includes a first valve moveably mounted in the main port for controlling water flow through the main port and a second valve moveably mounted in the secondary port for controlling water flow through the secondary port.

In addition, in various embodiments, another water sensing assembly is disclosed. The water sensing assembly is mountable on a water pipe and comprises a sensor, a generator, and a turbine coupled to the turbine and positionable through a bore in the water pipe into water flow within the water pipe.

The present disclosure also describes a method of sensing a property of water within a water distribution system. The method comprises a step of periodically sampling water within a water distribution system according to a sampling rate such that multiple water samples are obtained during each of at least one predefined logging interval. The method also includes the steps of measuring a property of the water for each of the multiple water samples and storing a maximum of two values of the measured property for each predefined logging interval, wherein the two values include a highest value measured and a lowest value measured.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIG. 3A is perspective detail view of the shape of a vertical axis turbine, according to various embodiments of the present disclosure.

FIG. 3B is a perspective view of a second water sensing assembly, according to various embodiments of the present disclosure.

FIG. 3C is cutaway side view of the second water sensing assembly of FIG. 3B, according to various embodiments of the present disclosure.

FIG. 11 is a screen view of a user interface for enabling a user to sign in with a server, according to various embodiments of the present disclosure.

FIG. 15 is a screen view of a user interface for enabling a user to edit parameters of a sensing device, according to various embodiments of the present disclosure.

FIG. 18 is a screen view of a user interface for enabling a user to edit user information, according to various embodiments of the present disclosure.

DETAILED DESCRIPTION

The present disclosure describes systems and methods for measuring properties of water within a water distribution system at multiple locations throughout the water distribution system. The present disclosure also describes sensors that may be installed in the water distribution system for one or more clients (e.g., water utility companies). The sensors may be configured to generate energy from the water itself to power its internal circuitry. The sensors may be tapped into the side of a pipe or installed at any location in the system.

The water property measurements may be logged in the sensors and periodically uploaded to a server using a wireless communication network. Measurements may also be uploaded on demand in some embodiments. The server, which may be a web server, maintains the measurements in a database. Clients may access the measurements to view the readings during various time periods. Also, the clients may request a substantially real-time measurement.

Figure 1A:
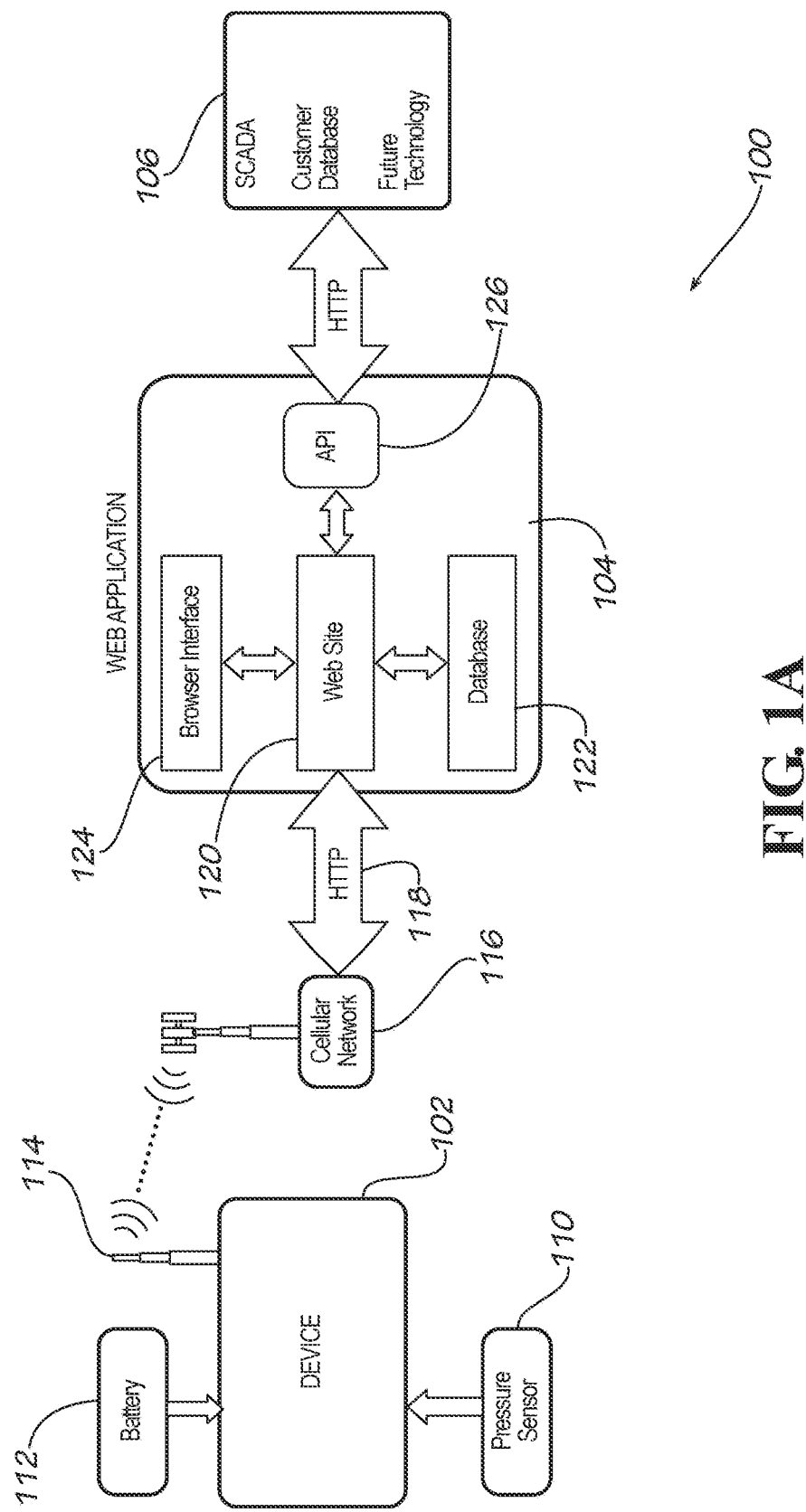
FIG. 1A is a block diagram illustrating a system for measuring properties of water in a water distribution system and managing the measurement data, according to various embodiments of the present disclosure.

FIG. 1A is a block diagram illustrating an embodiment of a system 100 for managing data related to properties of water in a water distribution system. As shown in this implementation, the system 100 comprises a sensing device 102, a web application 104, and a client system 106. It may be noted that, as illustrated, the system 100 includes a single sensing device 102 and a single client system 106. However, it will be understood by one of skill in the art that the system 100 may include any number of sensing devices 102 installed in various locations in the water distribution system. Also, the system 100 may include any number of client systems 106 for any number of clients. The multiple client systems 106 may be connected to the web application 104 through a communication network. In this respect, multiple sensing devices 102 may be used to monitor water properties at various locations within one or more water distribution systems for multiple clients, and the clients can access their respective sensor readings through the web application 104.

The sensing device 102 of the current embodiment comprises, among other things, a sensor 110 (e.g., a pressure sensor), a battery 112, and an antenna 114. The sensing device 102 may include any suitable type of sensor 110 for sensing various characteristics of water within a water distribution system. For example, the sensor 110 may be a pressure sensor for measuring water pressure at a particular location in the water distribution system, a flow rate sensor for measuring the rate that water is flowing through the particular location of the water distribution system, a chlorine sensor for measuring the chlorine content of the water at the location, or other types of sensors.

The battery 112 may include any suitable type of battery or batteries for providing power to the sensor 110 and other electronics of the sensing device 102. In some embodiments, the sensing device 102 may include a power generation device that harvests energy from the flow of water. The power generation device may be configured to recharge the battery 112, supplement the power of the battery 112, or even replace the battery 112.

The antenna 114 is configured to wirelessly transmit properties of water that are sensed by the sensing device 102 to the web application 104. The sensor data may be transmitted over any suitable type of wireless network 116, such as, for example, a cellular network, radio frequency (RF) channels, Wi-Fi, Bluetooth, etc. A receiver on the wireless network 116 is configured to convert the sensor data signals to allow transmission over a data network 118 using any suitable protocol, such as the Hypertext Transfer Protocol (http), Transmission Control Protocol (TCP), Internet Protocol (IP), or other communication protocol. The data network 118 may include a wide area network (WAN), such as the Internet, and/or may include local area networks (LANs).

The web application 104 as shown in FIG. 1A may be configured on a server, such as a web server, or a group of servers. The web application 104 may be associated with a data management company that provides a service to its clients for managing the clients' sensor data. For example, multiple clients (e.g., water distribution companies) may wish to have the data management company monitor the sensor data and then make the data available to the clients as desired. As explained in more detail below, the clients can customize how the water properties for the pipes in their system are to be sensed. They can also customize how the information about the sensor data can be accessed. They can also customize how they will be contacted if the sensor data reveals a warning or critical condition. In FIG. 1A, only one client system 106 is shown, but it should be understood that multiple client systems 106 may be configured in the system 100 to access the server on which the web application 104 is running.

Figure 1B:
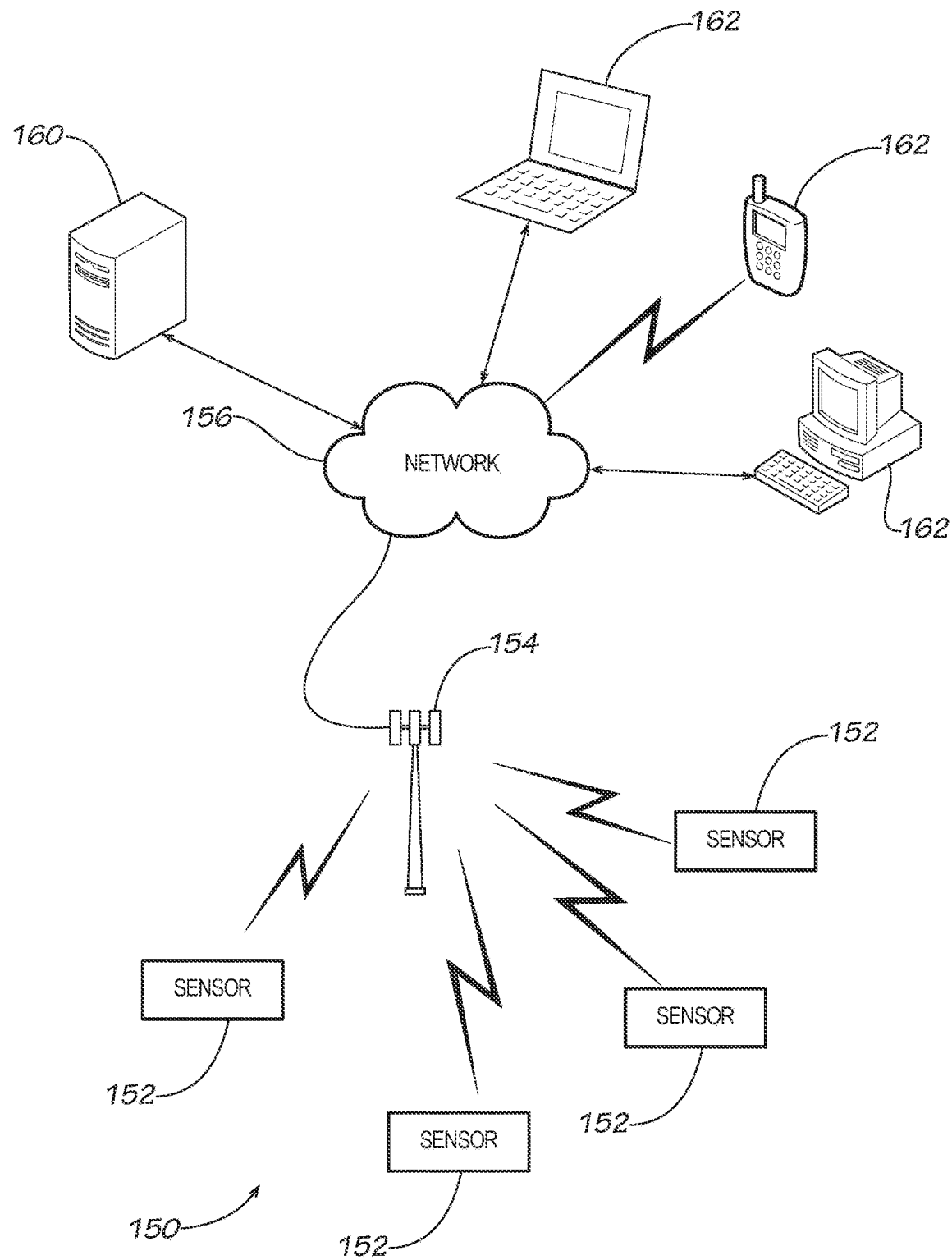
FIG. 1B is a block diagram illustrating a system for measuring properties of water and managing the measurement data, according to various embodiments of the present disclosure.

FIG. 1B is a block diagram illustrating an embodiment of a system 150 for measuring properties of water and managing the measurement data. According to the embodiment shown in FIG. 1B, the system 150 includes a plurality of sensing devices 152 that are distributed throughout an area and are installed to be in contact with water within a water distribution system. The sensing devices 152 are installed and put into service to allow them to take measurements of the water at their particular location and wirelessly communicate the measurement data to a cell tower 154 or other wireless communication device for receiving wireless signals, such as a Wi-Fi or Bluetooth receiver. Also, multiple cell towers 154 or receivers may be incorporated in the system 150.

The system 150 of FIG. 1B also includes a network 156, which enables communication from a wireless communication protocol, or other communication channel protocol, to a data network protocol. The network 156 enables the measurement data received by the cell tower 154 to be transmitted to a server 160. The server 160 may be one or more computer systems for managing the measurements of water properties. The server 160 may be a web server for providing a web site for clients to access if authorized. The system 150 also includes client devices 162, which may include desktop computers, wired or wireless laptop devices, smart phones, or other computer system. The client devices 162 may include computer systems for any number of clients. Also, it should be known that any number of client devices 162 may be used for each client.

Figure 1C:
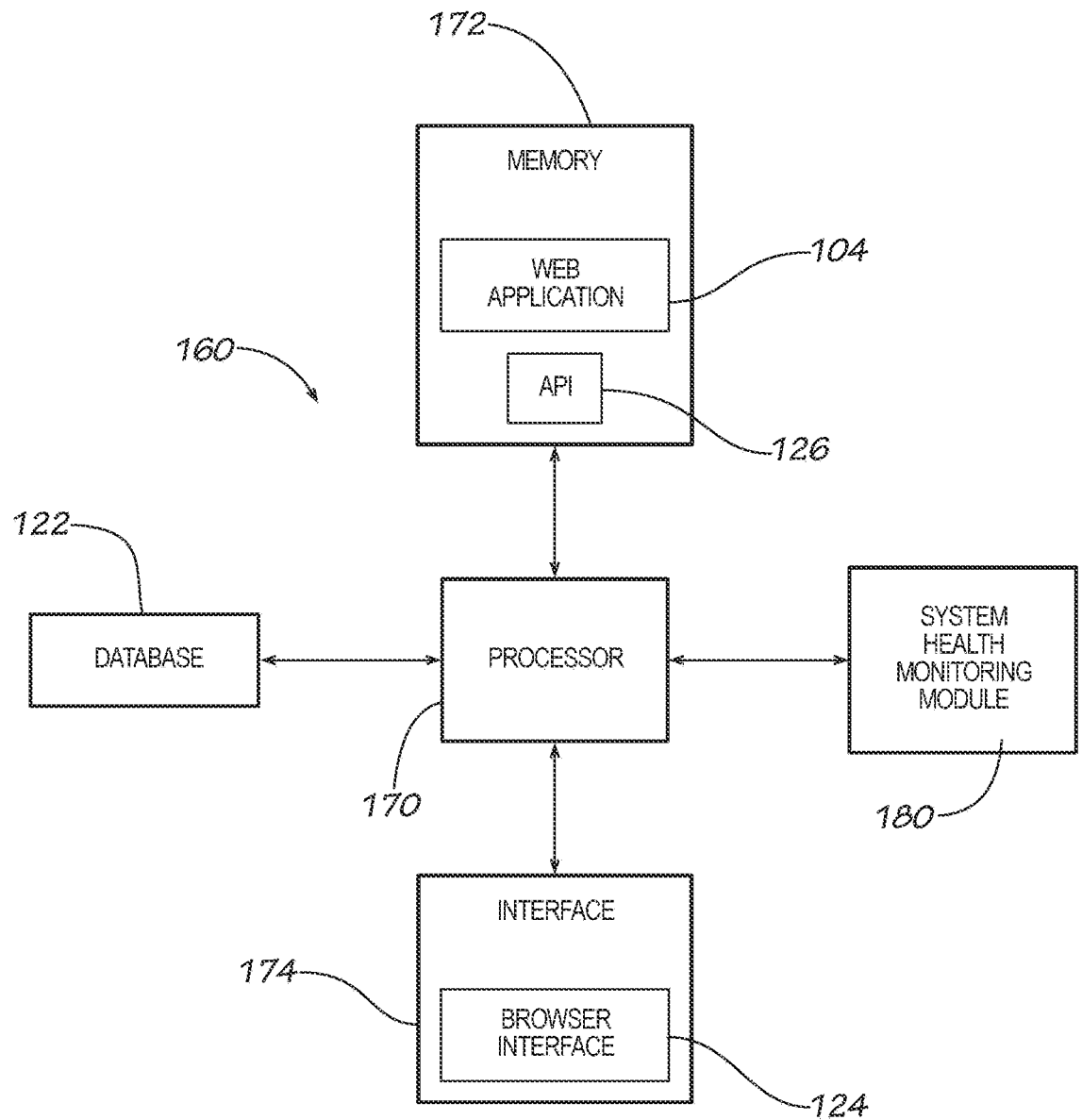
FIG. 1C is a block diagram illustrating the server shown in FIG. 1B, according to various embodiments of the present disclosure.

FIG. 1C is a block diagram of an embodiment of the server 160 shown in FIG. 1B. In this implementation, the server 160 comprises a processor 170, a memory 172, an interface 174, and the database 122. In some embodiments, the database 122 may be separate from the server 160. The processor 170 is configured to control the operations of the server 160. The server 160 may execute certain functions that may be stored in software and/or firmware and execute functions that may be configured in hardware. The memory 172, in some embodiments, may comprise the web application 104 and the API 126. The interface 174, in some embodiments, may comprise the browser interface 124. The interface 174 may be a network interface for interfacing with the client devices 162 via the network 156.

The web application 104, according to the embodiment shown in FIG. 1A, may comprise at least a web site 120, a database 122, a browser interface 124, and an Application Programming Interface (API) 126. As shown in FIG. 1C, the web application 104, database 122, browser interface 124, and API 126 may be contained within the server 160. The web site 120 provides various web pages and screen views (as explained below) to a user on the client system 106 or client devices 162. The database 122 is configured to store the data retrieved from the sensing devices 102, 152. The database 122 may be arranged to securely separate the data for one client from another. In some embodiments, multiple databases 122 may be used. The browser interface 124 enables a user on the client system 106 to access the web site 120 and obtain sensor data formatted in an organized way, as described below. The API 126 provides an interface for the client system 106 to access the web application 104. The web application 104, with the web site 120, browser interface 124, database 122, and API 126, may be configured in one package, such as in a single server (e.g., server 160).

The web site 120 can take requests from authorized clients, search the database 122, and send information back to the clients. In some embodiments, the clients may wish to request a certain reading at a certain time and date. The log in the database 122 that is closest to that time and date can be retrieved from the database 122 and sent to the SCADA system.

Furthermore, the web site 120 may be configured to include two different types of retrieval techniques for the clients' use. The first technique is a simple Read, while the second technique is referred to ReadX. With Read, the client may make requests for data, and in response the data log is retrieved and sent back to the client. In this case, the data is merely read from the database 122 and remains in the database 122 without any change to the data entry.

However, a ReadX command allows a client to request data. Again, the data is retrieved and sent to the client. In this case, however, the web application 104 checks to ensure that the client has indeed received the data. For example, the API 126 may request for an acknowledgement from the client that the records were received successfully. When the client system 106 receives the data successfully and stores this data in its own database, it sends an acknowledgement (ACK) receipt back to the web application 104. When the API 126 receives this ACK receipt signal, the web application 104 erases that data from the database 122.

One benefit of the ReadX command, for example, is for security. Certain clients may not want their data to be stored on another database that does not belong to them. This may also be beneficial for the data management company that owns the server 160 or web application 104, because the owner may be released from any liability associated with the other party's information. In this respect, the client can be able to hide or manage their proprietary data any way they see fit.

The client system 106 or client device 162 may include any suitable communication device capable of transmitting and receiving http or other data transmissions. For example, the client system 106 or client device 162 may be a personal computer, laptop computer, tablet computer, or other computer systems. The client system 106 or client device 162 may also include portable electronic communication devices, such as cell phones, smart phones, or other mobile devices that may utilize a cellular network, data network, or other types of networks. The client system 106 or client device 162 may include its own database for storing sensor data retrieved from the web application 104. The client system 106 or client device 162 may be a Supervisory Control and Data Acquisition (SCADA) system. The client system 106 or client device 162 may also be configured to contain a user interface that allows a user to see web pages of the web application 104, as described below with respect to FIG. 11-18.

The system 100 may be a multi-tenant system for managing sensors for multiple clients. The system 100 may be configured to show only the sensor devices for each particular client when a client signs in. Thus, each client is only able to see their own sensors and not the sensor of other clients. However, a master device may be connected in the system 150 to allow a user to access information for all the sensors. The master device may be the server 160 that run the web application 104 or may be computer system connected directly to the server 160. In some respects, the master device may be operated by a city or county government for monitoring the water distribution systems in their jurisdictions.

The system 100 gives clients an inexpensive product that can be employed relatively easily on the part of the client. The system 100 allows a client (e.g., water utility company) to sign up with a service that provides a combination of water monitoring functions all in one package.

The server 160 associated with the web application 104 may be configured with a system health monitoring module 180. The system health monitoring module 180 may be configured in software, hardware, and/or firmware. The system health monitoring module 180 may be configured to evaluate the health of the water distribution system using an empirical method of analyzing many data points. The system health monitoring module 180 may be neural network for determining whether values are within a normal range. In some embodiments, the data points may be evaluated based on their location in the water distribution system and based on the time of day when the measurements were taken. The system health monitoring module 180 may use statistical analysis to determine if certain points are abnormal or unhealthy with respect to baseline data points established for a normal or healthy system.

In some embodiments, the system health monitoring module 180 may use the Mahalanobis-Taguchi System (MTS) for determining the health of the system. The MTS, for example, uses pattern recognition to analyze multivariate data. The system health monitoring module 180 can analyze values with respect to norms based on the MTS model. Not only does the MTS model diagnose the norms, but it can also include a predictive method for analyzing patterns in multivariate cases.

The system health monitoring module 180 may analyze both location-dependent and time-dependent data. For example, a water flow rate at 4:00 pm at a certain location in the water distribution system may have a certain normal range based on multiple measurements taken at this time. When values are outside of this range, the system health monitoring module 180 can instruct the interface 174 to provide an alert to the client. In some embodiments, the system health monitoring module 180 may process data stored in the database 122 from multiple sensors and consider all the parameters when diagnosing health.

The server 160 is also configured to read data in real time, perform hydraulic simulation in real-time, and recommend a pump power level in real-time. The server 160 may also read data, perform hydraulic simulation, and control the pump power level. The server 160 may also be configured to detect leaks in the main when the pressure matrix is abnormal.

Figure 2:
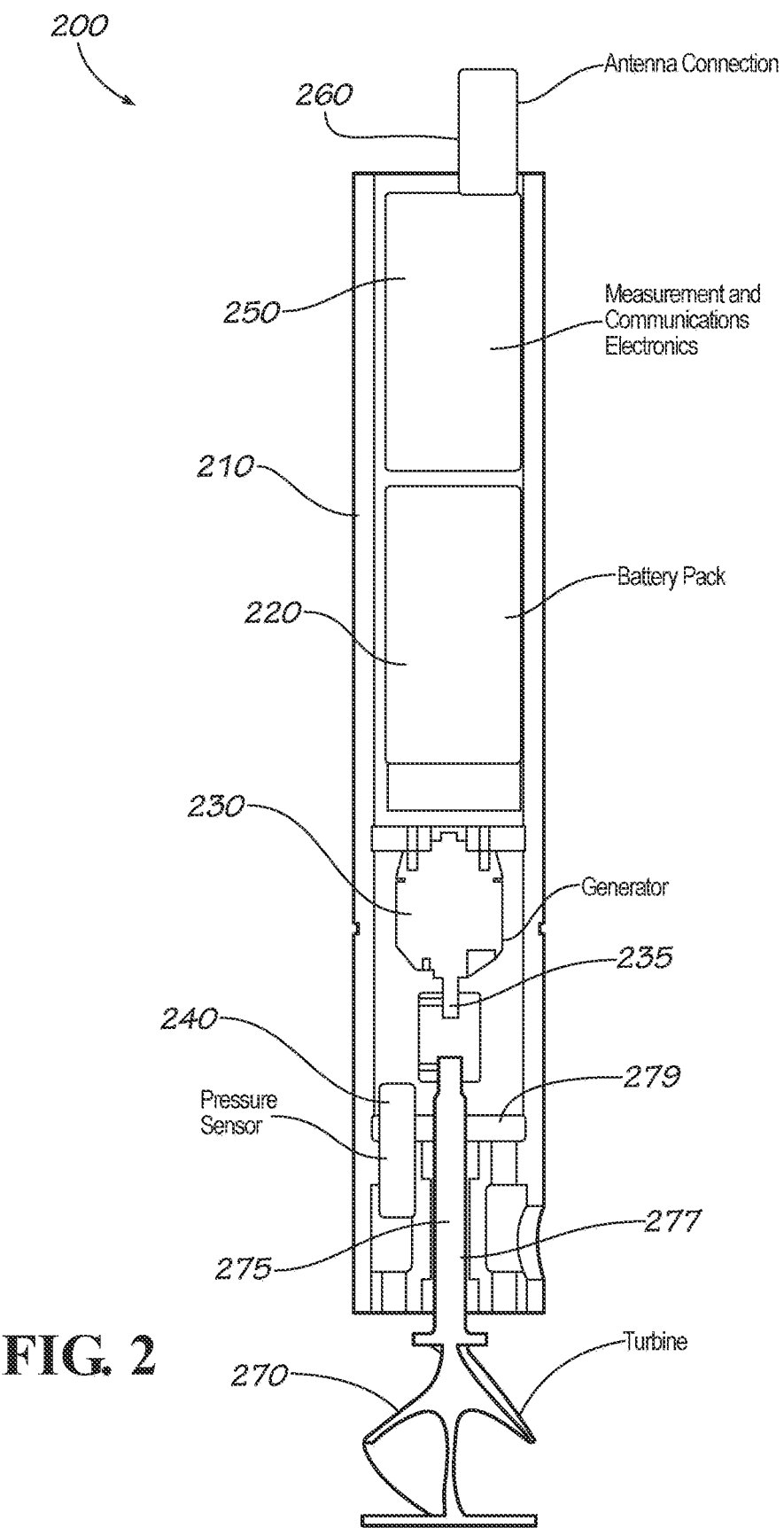
FIG. 2 is a cutaway side view of a water sensing assembly, according to various embodiments of the present disclosure.

FIG. 2 is a cutaway side view of a water sensing assembly 200, according to various embodiments of the present disclosure. The water sensing assembly includes a housing 210 enclosing a battery pack 220, a generator 230, a pressure sensor 240, and measurement and communication electronics 250. An antenna 260 is mounted to the exterior of the housing 210. Extending from a lower end of the housing 210 is a turbine 270. The turbine 270 is a vertical axis turbine in the current embodiment, and is coupled to the generator 230 by a turbine shaft 275 extending through a sealed shaft bore 277 and a seal partition 279 to connect with a generator shaft 235 of the generator 230. In various embodiments, the turbine 270 is may be indirectly coupled to the generator, such as with magnets, so that the turbine 270 may be fully separated from a sealed interior of the housing 21.

The pressure sensor 240 is mounted within the housing 210 such that the pressure sensor 240 extends through the seal partition 275 to partially expose pressure sensor 240 to fluid flow along the lower end of the housing 210, which may travel around turbine 270 into the lower interior of housing 210. The pressure sensor 240 communicates fluid pressure readings to measurement and communications electronics 250, which may process, store, and/or communicate the date through antenna connection 260. The measurement and communications electronics 250, pressure sensor 240, and antenna 260 are powered by battery pack 220, which is recharged by generator 230.

In operation, the water sensing assembly 200 is a self-contained, removable sensing unit that may be tapped into a fluid pipe or other valve through a tap or bore. The turbine 270 is situated such that the turbine 270 is within the fluid path of the fluid passing through the fluid pipe. The fluid flow thereby turns the turbine 270, turning the generator shaft 235, causing the generator 230 to generate a current to recharge batter pack 220. The presence of the turbine 270 and generator 230 attached to the battery pack 220 allows the battery pack 220 to last longer, giving the water sensing assembly 200 a longer life to detect sensing data. The pressure sensor 240 may be replaced by various other sensors in various embodiments, such as chlorine or flow sensors.

FIG. 3A is detail view of the shape of a vertical axis turbine 370. As seen in FIG. 3A, the vertical axis turbine 370 includes two wings 372a,b, each wing having a curved profile and extending in opposite spirals on either side of a central turbine axis 374. When fluid flows in against vertical axis turbine 370 in a direction 376 orthogonal to the central turbine axis 374, fluid pushes wings 372a,b such that the vertical axis turbine 370 spins about central turbine axis 374.

FIG. 3B is a perspective view of a second water sensing assembly 300, according to various embodiments of the present disclosure. The water sensing assembly 300 includes a housing 310, a mounting bracket 320, mounting bracket fasteners 325, power wires 330, and a turbine 340. As seen in FIG. 3B, the housing 310 is coupled to the mounting bracket 320, and power wires 330 extend through a wiring bore 322 defined in the mounting bracket 320 into housing 310.

FIG. 3C is another cutaway side view of the second water sensing assembly 300 of FIG. 3B, according to various embodiments of the present disclosure. As seen in FIG. 3C, a generator 350 is mounted within the housing 310 similarly to generator 230. The turbine 340 extends from a lower end of the housing 310 similarly to turbine 270. The turbine 340 is a vertical axis turbine in the current embodiment, and is coupled to the generator 340 by a turbine shaft 345 extending through a sealed shaft bore 347 and a seal partition 349 to connect with a generator shaft 355 of the generator 350. A side bore 380 is defined in the housing 310 below seal partition 349 so that fluid may flow around turbine 340 to side bore 380. In various embodiments, the turbine 340 is may be indirectly coupled to the generator, such as with magnets, so that the turbine 340 may be fully separated from a sealed interior of the housing 310. In the current embodiment, the power wires 330 may be directly connected to the generator to power sensing, communication, process, data storage, and other electronic equipment. Further, a pressure sensor or other sensor may be mounted within the housing 310 similarly to pressure sensor 240 within housing 210.

The mounting bracket 320 may mount the water sensing assembly 300 on any sort of sensing, tapping, or boring equipment.

Figure 4:
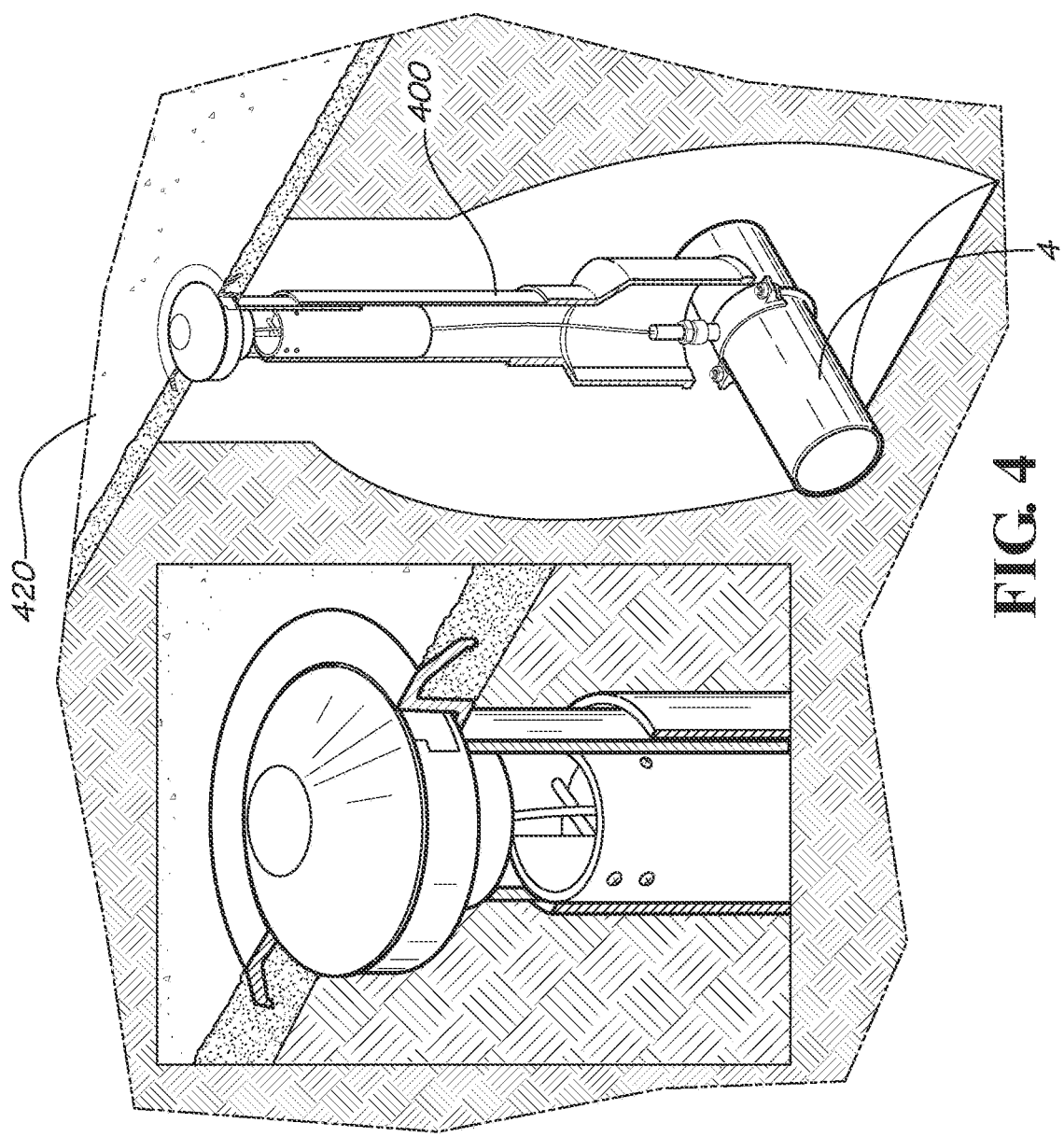
FIG. 4 is a diagram of a third water sensing assembly installed on a pipe, according to various embodiments of the present disclosure.

FIG. 4 is a diagram of the water sensing assembly 400 of FIG. 2 installed on a pipe, with various partial cross-sectional views of parts of the water sensing assembly 400 and the surrounding environment, according to various embodiments of the present disclosure. The water sensing assembly 400 is buried underground in the current embodiment such that it extends from a pipe 410 to a ground surface 420, such as a road.

Figure 5:
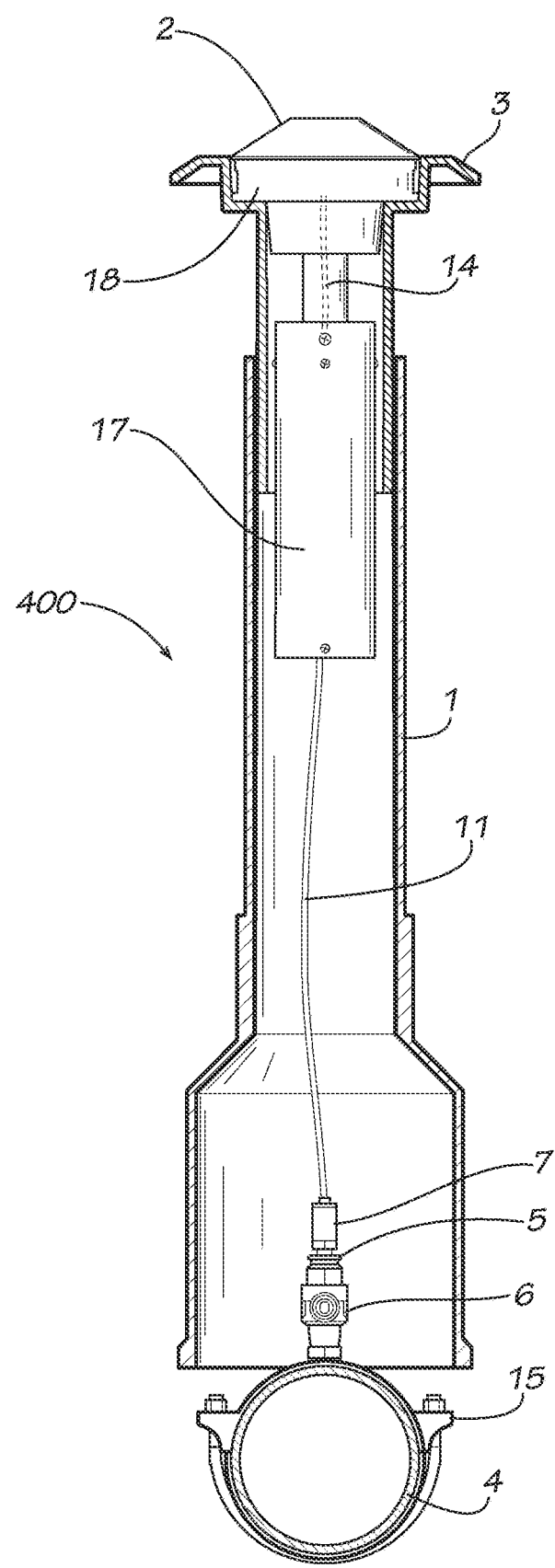
FIG. 5 is front cross-sectional view of the third water sensing assembly of FIG. 4, according to various embodiments of the present disclosure.

FIG. 5 is front cross-sectional view of the water sensing assembly 400 of FIG. 4, according to various embodiments of the present disclosure. As seen in FIG. 5, the water sensing assembly 400 includes a valve box 1 mounted over pipe 4. A saddle 15 connects ball valve 6 to the pipe 4, and a reducer 5 couples a pressure sensor 7 to the ball valve 6. Wiring 11 runs up through the valve box 1 to a communication assembly 17. The communication assembly 17 may contain processing, data storage, and power equipment in various embodiments to store, communicate, and receive orders based on data received from the pressure sensor 7. To communicate data and receive orders, the communication assembly 17 is connected by a wire 14 to an antenna 2 mounted on an iron cap 18, the iron cap 18 itself mounted on an adjustable top 3. The adjustable top 3 connects to the valve box 1, forming an enclosure extending from ground surface 420 to the top of pipe 410 to protect the enclosed equipment. The adjustable top 3 can be adjusted telescopically to vary the overall height of the water sensing assembly 400, based on the depth of the pipe below ground level. Other sensors may be used with water sensing assembly, such as chlorine or flow sensors.

Figure 6:
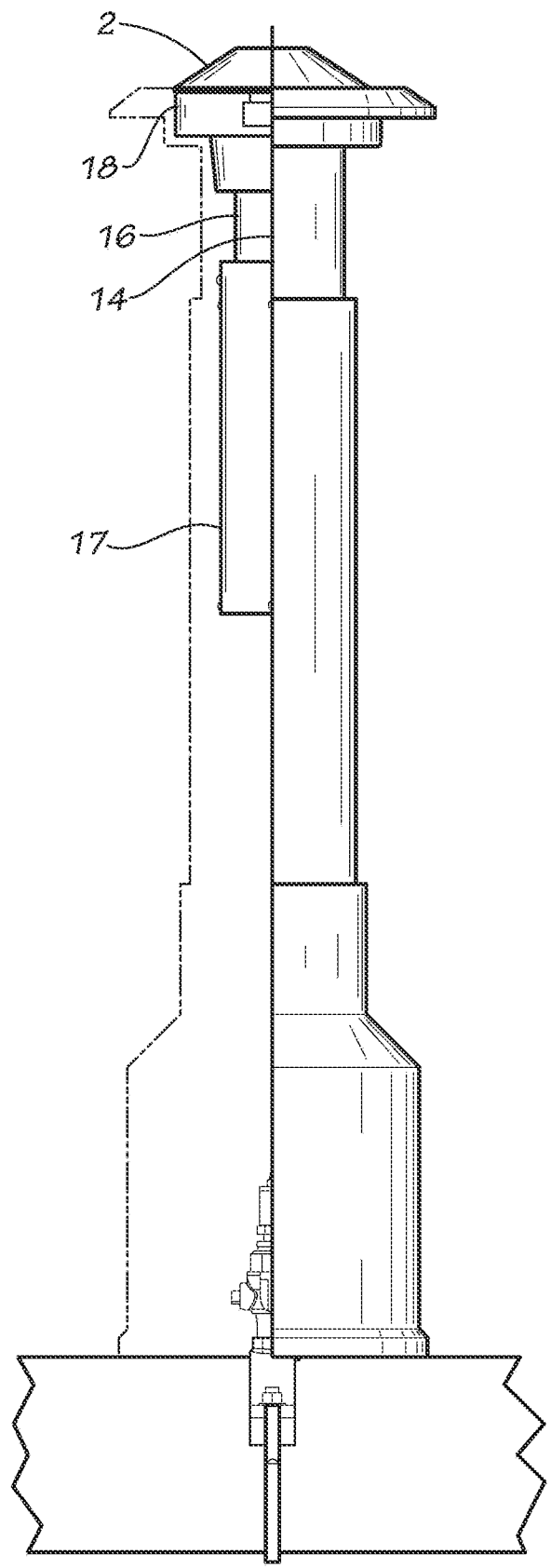
FIG. 6 is a partial cross-sectional side view of the third water sensing assembly of FIG. 4, according to various embodiments of the present disclosure.

FIG. 6 is a partially cutaway side view of the water sensing assembly 400 of FIG. 4, according to various embodiments of the present disclosure. As seen in FIG. 6, the communication assembly 17 is mounted to the iron cap 18 by a hanging bracket 16. The communication assembly 17 is configured to receive measurement signals from the and transmit the signals from antenna 2 of the sensor assembly. The signals are transmitted to the web application 104 via the cellular network 116 or 154. The antenna 2 may be configured for Global System for Mobile (GSM) communication using a cellular network, Code Division Multiple Access (CDMA) communication, or can be used with other types of communication networks and protocols. In some embodiments, the communication device 17 may include a plug-in for Wi-Fi, Bluetooth, or other short range communication.

Figure 7:
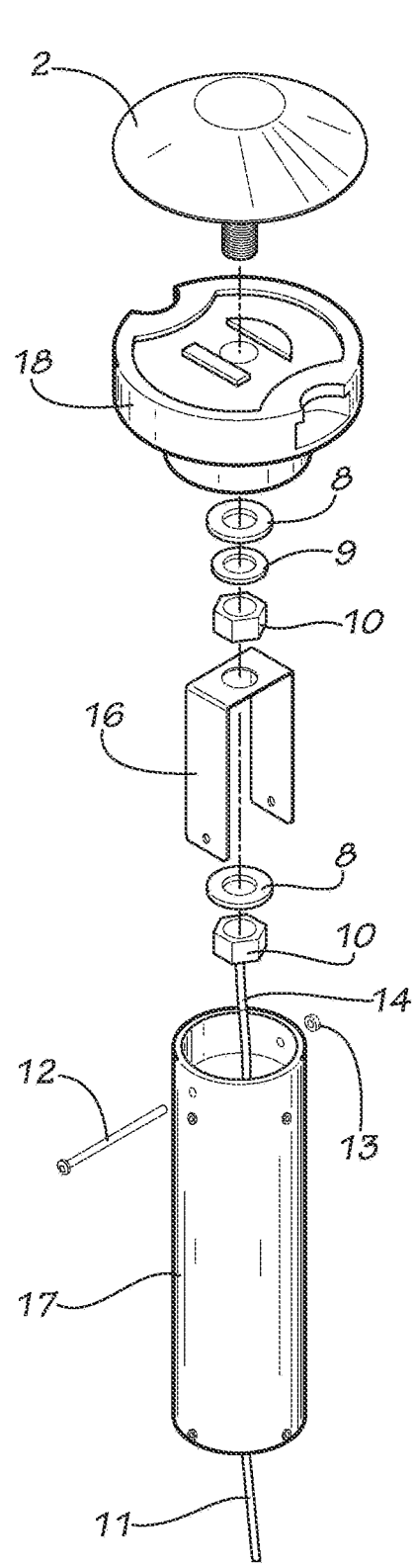
FIG. 7 is an exploded view of a communication assembly of the third water sensing assembly of FIG. 4, according to various embodiments of the present disclosure.

FIG. 7 is an exploded view of the water sensing assembly 400 of FIG. 4, according to various embodiments of the present disclosure. As shown in FIG. 7, the water assembly 400 includes two flat washers 8, lock washer 9, two hex nuts 10, hanging bracket 16, machine screw 12, and jam nut 13, the combination of which mounts communication assembly 17 to iron cap 18.

Figure 8:
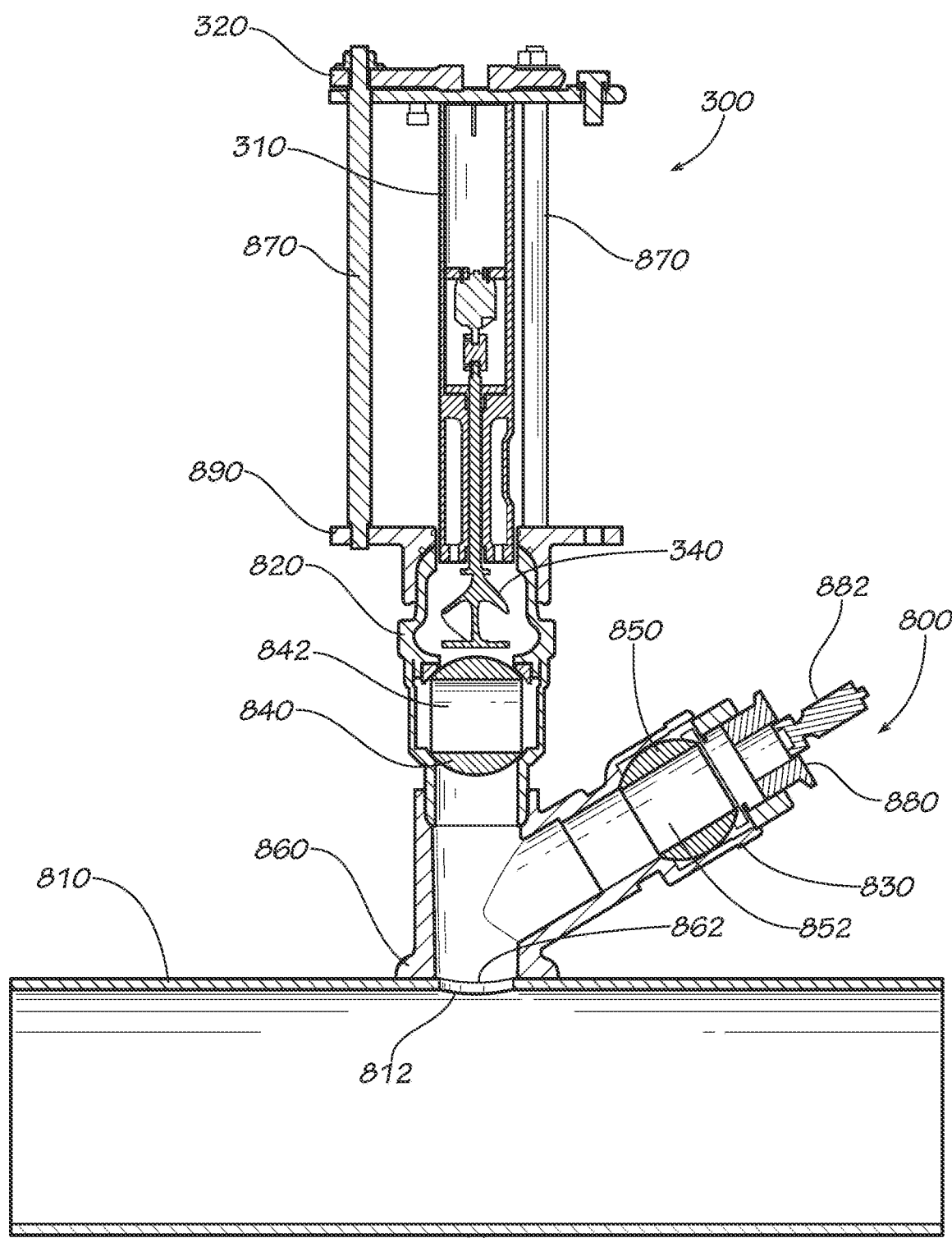
FIG. 8 is a cutaway side view of a water sensing assembly of FIG. 3B in a multi-port service saddle, according to various embodiments of the present disclosure.

FIG. 8 is a cutaway side view of a water sensing assembly 300 mounted in a multi-port service saddle 800 on a pipe 810, according to various embodiments of the present disclosure. As shown in FIG. 8, the multi-port service saddle 800 includes a main port 820 and a secondary port 830. A ball valve 840 is mounted in main port 820 and a ball valve 850 is mounted in secondary port 830. Ball valve 840 includes a ball bore 842 and ball valve 850 includes a ball bore 852, each of which may be turned to open and close main port 820 and secondary port 830, respectively. In FIG. 8, the ball valve 840 is closed and the ball valve 850 is open.

A lower end 860 of the multi-port service saddle 800 defines a lower opening 862, which is aligned with a bore 812 in the pipe 810.

To form bore 812 in the pipe 810 without leakage from the pipe, the multi-port service saddle 800 is mounted to the pipe exterior with the ball valve 840 open and the ball valve 850 closed. A tapping machine is mounted to main port 820 and is pushed down through main port 820 to form bore 812. The tapping machine is then pulled out of ball valve 840 into a pre-insertion position and ball valve 840 is closed. Water sensing assembly 300 may then be mounted to multi-port service saddle as shown in FIG. 8.

As shown in FIG. 8, water sensing assembly 300 is mounted to a port bracket 890 coupled to main port 820. Insertion screws 870 extend between mounting bracket 320 and port bracket 890, with turbine 340 and housing 310 pre-inserted into main port 820. A sensor cap 880 is shown coupled to secondary port 830 and including a sensor 882. Sensor 882 can be any sensor for fluid data collection, such as a pressure sensor, chlorine sensor, or flow sensor. While the water sensing assembly 300 is mounted outside ball valve 840, fluid may flow into multi-port service saddle 800 to secondary port 830 where the fluid may be sensed by sensor 882.

Figure 9:
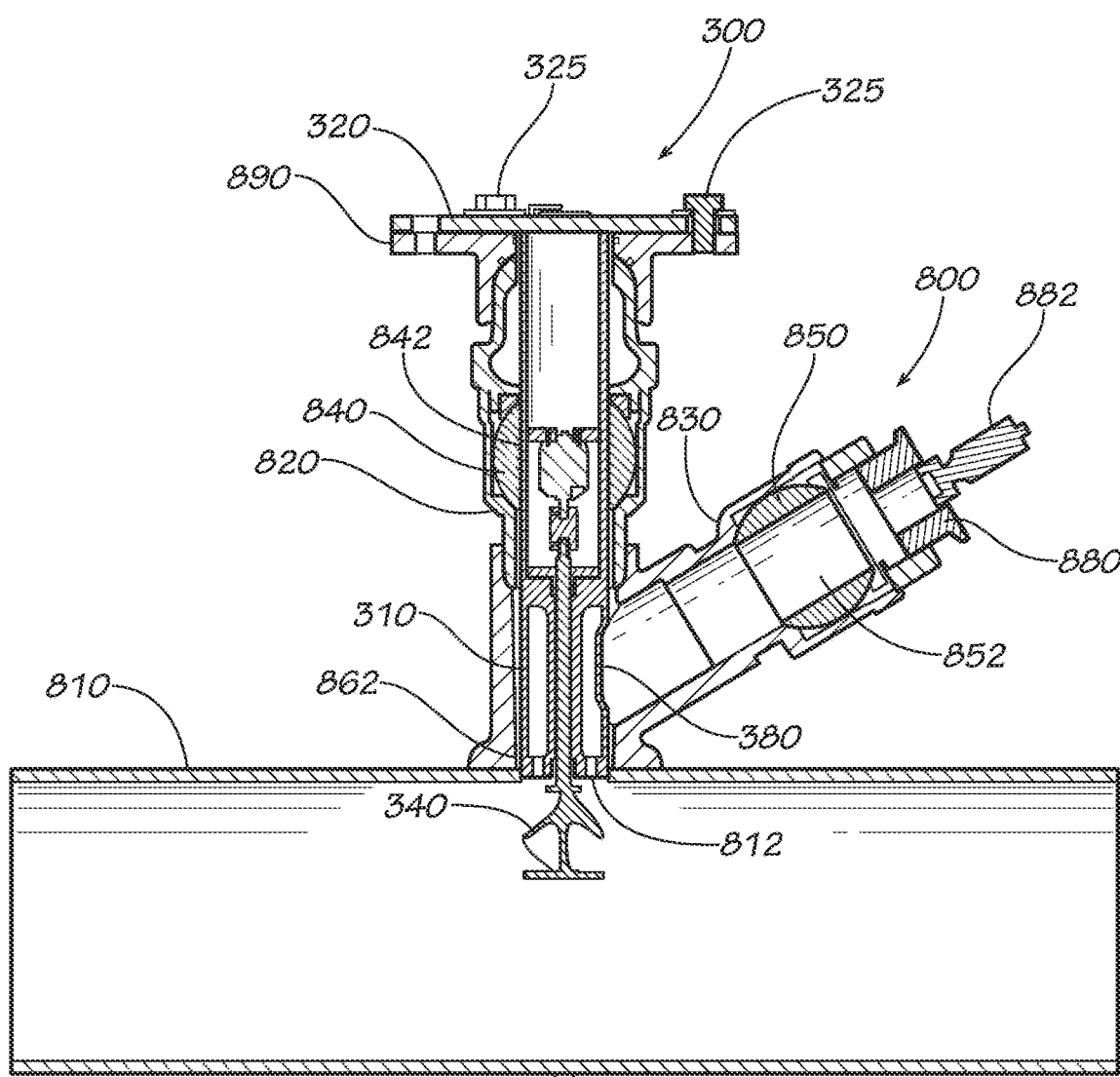
FIG. 9 is a cutaway side view of the second water sensing assembly of FIG. 3B in the multi-port service saddle of FIG. 8 in a power generation mode, according to various embodiments of the present disclosure.

FIG. 9 is a cutaway side view of the second water sensing assembly 300 in a power generation mode, according to various embodiments of the present disclosure. To place water sensing assembly 300 in power generation mode, ball valve 840 is opened and insertion screws 870 are tightened to pull mounting bracket 320 towards port bracket 890. Once mounting bracket 320 and port bracket 890 are flush together, as shown in FIG. 9, mounting bracket fasteners 325 fasten mounting bracket 320 to port bracket 890. However, in various embodiments, water sensing assembly 300 may be inserted to various degrees within main port 820 such that turbine 340 may be partially presented at varying depths to fluid flow within pipe 810, which may lessen the speed at which turbine 340 turns, generating less power and allowing for a customizable level of power generation based on known fluid flow and power needs. Moving mounting bracket 320 towards port bracket 890 inserts housing 310 and turbine 340 into main port 820 such that turbine 340 extends down through lower opening 862 bore 812 into fluid flow within pipe 810, thereby turning turbine 340 and generating current to power various equipment or recharge batteries. In this configuration, fluid flow may pass up through side bore 380 so that sensor 882 may continue to sense fluid conditions within pipe 810. Turbine 340 may be removed from the fluid path within pipe 810 by use of insertion screws 870 to move mounting bracket 320 away from port bracket 890. This may be necessary if, for instance, a pig is sent down the pipe 810 to clean the system and it is desired to prevent damage to turbine 340.

Figure 10:
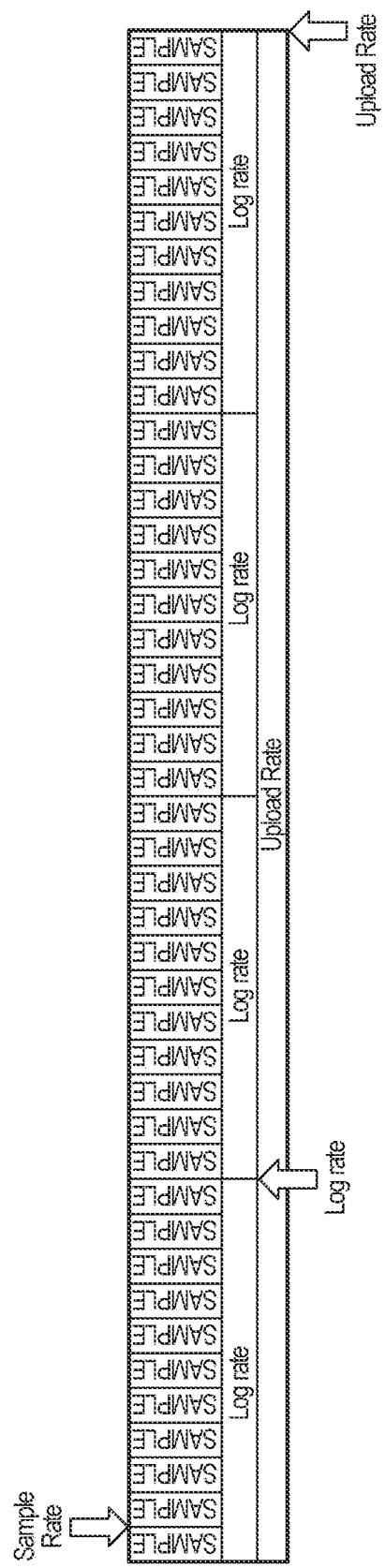
FIG. 10 is a chart showing sampling rate, log rate, and upload rate, according to various embodiments of the present disclosure.

FIG. 10 is a chart showing an exemplary sampling rate, log rate, and upload rate related to sensing water properties. The sensing assembly may be configured to remain in a sleep mode until it is configured to wake up and take a sample reading. For example, the sampling rate may include sampling once every 15 seconds. The log rate may be set, for example, at about once every 15 minutes. During the log interval (e.g., 15 minutes), the processing device of the sensor assembly may be configured to store only the samples that are the highest value and the lowest value. Measurements in between the high value and low value during that log interval may be discarded. When a new high or new low value is sampled, it replaces the old value. In this sense, only two values are stored during each log interval. At the end of the log interval, the processing device stores the high and low value for that interval in memory. Therefore, at the log rate (e.g., once every 15 minutes), two values are stored or logged. The sensor assembly repeats the logging at the log rate until it is time for uploading as determined by the upload rate. In one example, the upload rate may be about once per day. This is the rate at which the sensor assembly uploads the log information via the antenna 114 to the server 160.

One benefit of these three rates is that the sensor data does not consume much memory within the sensor assembly, only the high and low values for each log interval. Also, the upload rate may be set to upload not very often (e.g., once a day), which can conserve battery life versus uploading after every reading. Thus, the sensor and communication device 17 may be in a sleep mode and then wake up only to sense and upload data. For example, with these rate settings, a battery may last about seven years or longer.

In some embodiments, the sampling rate and log rate may be set to the same rate. A client may request such a set-up if they wish to view the data in more detail and have access to the data at any time. The cellular modem may be placed in a low-power mode and listen for a signal, such as an SMS message from the client. In this way, the client can get a substantially real-time measurement. When requested in this manner, the sensor assembly is waken up, regardless of the sampling rate times, and takes a reading. The communication device sends the newly taken reading, or, in some embodiments, may send the high and low readings of a current logging interval, to the web application 104. The web site 120 can then communicate that data directly to the client, via e-mail, SMS, or other communication channel. Of course, this strategy may increase the battery usage compared with normal operations. This may cut the battery life to about two years.

The client may be given options to choose between different types of plans for receiving sensor data. For example, the client may wish to have access to data under normal operations, with the uploaded data being available the following day. The second option may be the substantially real-time plan.

Another feature of the sensor assembly is that when sample data is measured, the processing device may analyze the data to see if it falls within a normal range of values. If so, then nothing needs to be done, except store the values if they are highs or lows for the period. Otherwise, if the values are not within normal range, the communication device sends an alert to the web site 120. In this case, the modem is waken from sleep mode and instructed to transmit the details of the out-of-range measurement. In response to receiving this alert, the web site 120 may be configured to check the reading with the client's settings to find out what type of notification they wish to receive when such a condition occurs. The web site 120 may then send an SMS message, e-mail, or other type of message to inform the client of the condition.

FIGS. 11-18 show examples of various screen views of web pages that may be displayed on a user interface, such as the user interface of the client system 106. The web pages may be part of the web site 120 shown in FIG. 1 that allows a client to access the data stored in the database 122. The web pages are designed to provide an organized and easy to understand display for the users.

Figure 11:
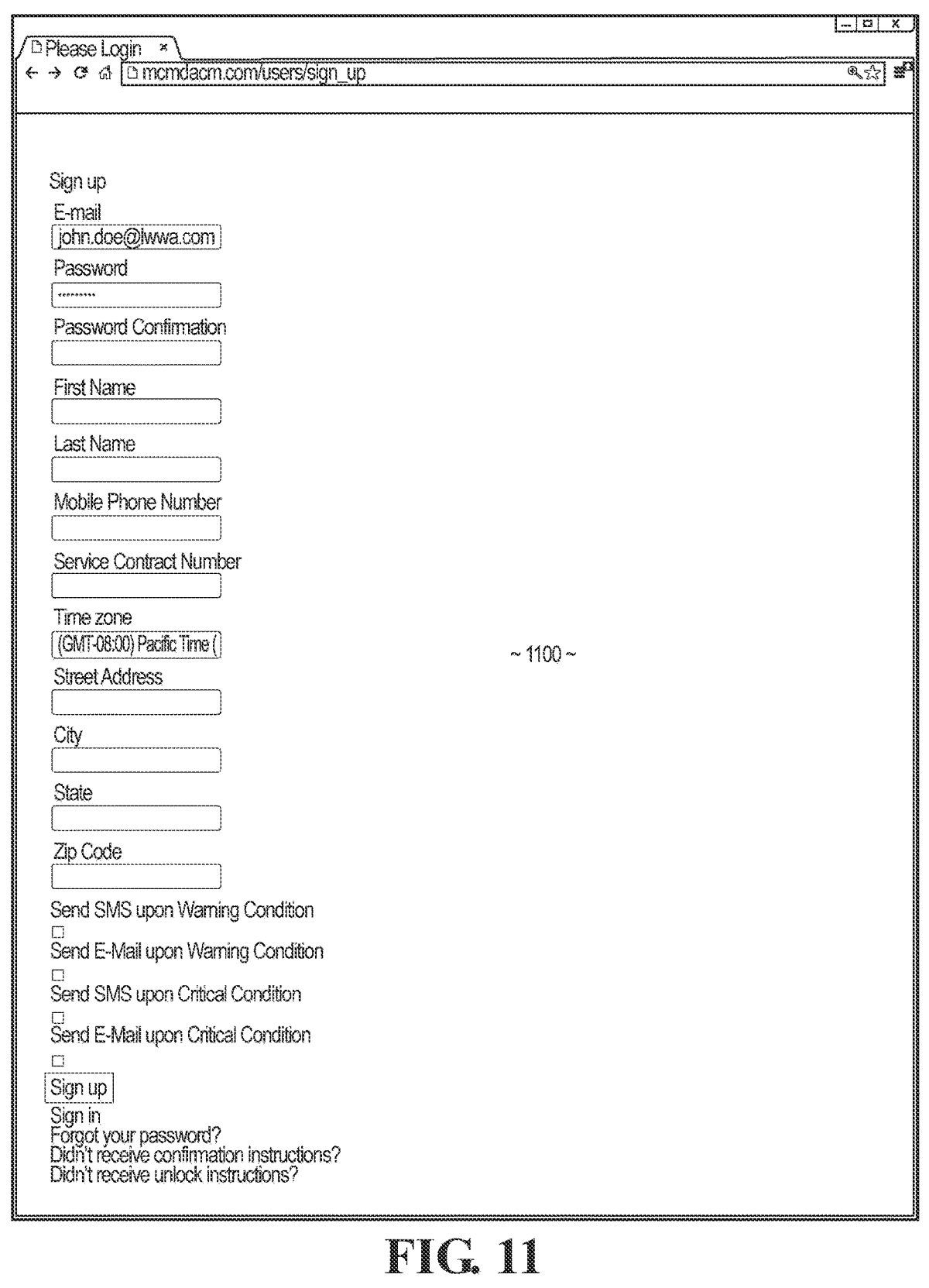

FIG. 11 is an example of a screen view of a web page that may be displayed on a user interface 1100 for enabling a user to sign up to receive a service for viewing water property data. Initially, a new user signs up or registers with the web server. After the user is registered, he or she can sign in to the server and obtain the relevant data. For example, the web server may include the one or more web servers that are configured to run the web application 104 shown in FIG. 1. In this respect, the user interface 1100 may be displayed on a screen, display, monitor, or other visual indication device of the client system 106. The user interface 1100 allows a user to sign up using an e-mail address, password, first name, last name, and mobile phone number.

Also, the sign up user interface 1100 includes an entry window for a "service contract number." The service contract number is a number that is set up for a particular client that has a service contract with the company that manages the web application 104 shown in FIG. 1. A client may allow its associates or employees to also sign up to gain access under the respective service contract number.

The user interface 1100 also includes entry windows for time zone, street address, city, state, and zip code. This can be the information for the location of the client (e.g., water distribution company).

In addition, the user interface 1100 includes four selectable boxes that allow the new user to set up the types of ways that the user may be contacted if a warning condition or critical condition occurs. For example, the user may choose to receive a text message (e.g., a Short Message Service (SMS)) message or other type of electronic message on a portable electronic device. The user may also choose to receive an e-mail message for warning or critical conditions. For example, a warning condition may be a condition that if untreated may lead to problems with the water distribution system, while a critical condition may be a condition that indicates a more severe problem, such as pipe that has burst.

One method for initiating a new contract according to one implementation may include the following. The data managing company provides a service contract number to a new client. They also send the client a URL and instructions on how to set up an account. The URL and instructions are contained in an e-mail that is sent to the client. A contact person (e.g., a boss) at the client's company may set up a profile for himself or herself. He or she may also send the URL and instructions to other in the company so that they too can set up a profile. The additional profiles will include the personal information for the other people (e.g., employees) and will also include the same service contract number for that company. Each individual in the company can therefore choose the types of notifications they receive when a warning condition or critical condition is sensed.

Figure 12:
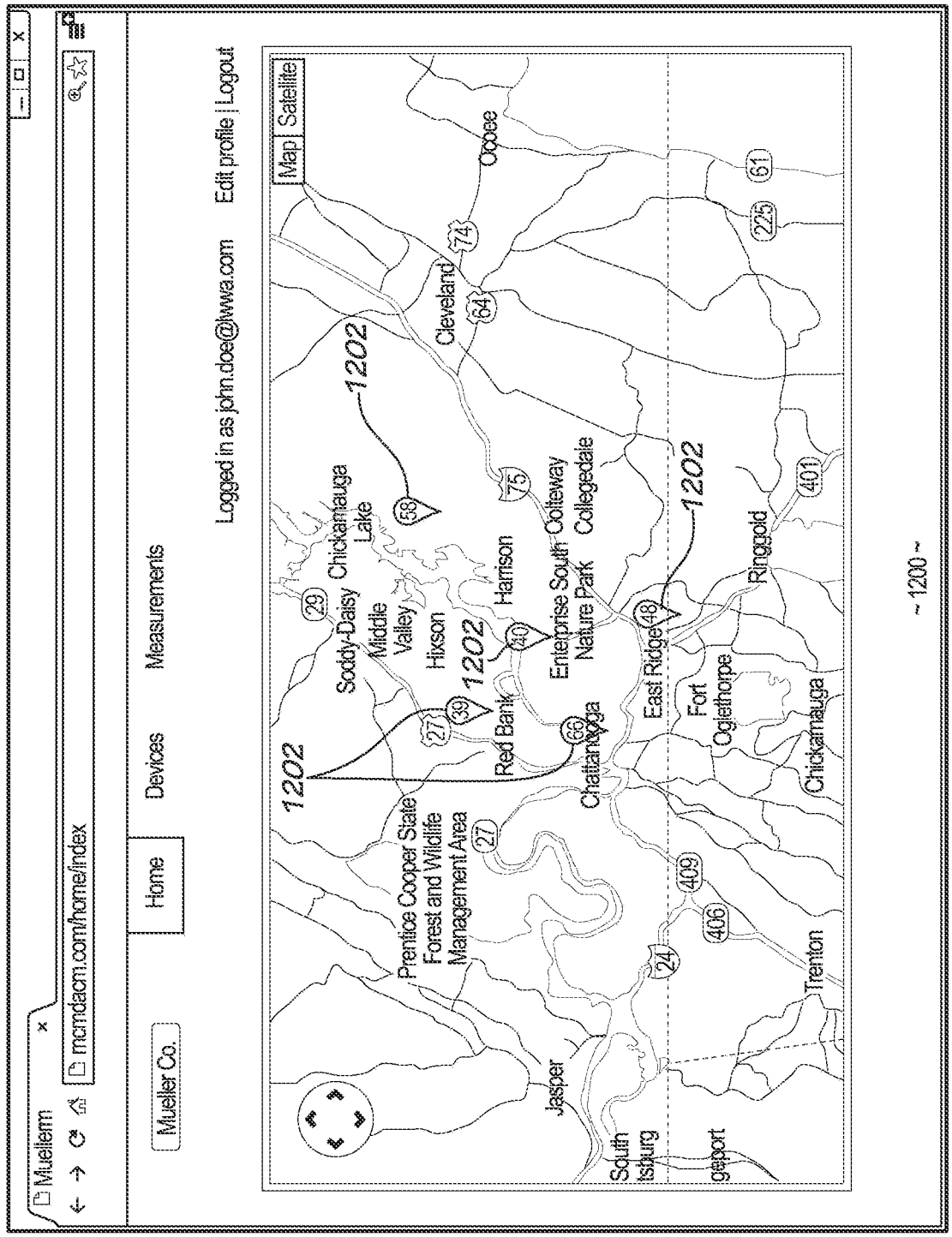
FIG. 12 is a screen view of a user interface showing a map of the locations of installed sensors, according to various embodiments of the present disclosure.

FIG. 12 is an example of a screen view of a web page that may be displayed on a user interface 1200 showing a map of sensing device locations. The map may be any suitable map of an area where a client's sensing devices are installed. Sensors may be installed in any part of the water distribution system, such as on main pipes, secondary pipes, neighborhood pipes, residential pipes, etc. For example, the map may be provided by Google Maps or other online mapping service.

Superimposed on this map are icons 1202, which are configured to display the locations of the sensor devices 102. As shown in this figure, five icons are displayed, representing five different sensor devices 102. It should be understood that the map may show any number of icons 1202, depending on how many sensor devices are installed and placed in service. The icons 1202 can each include a number for distinguishing one sensor from another. If a user selects one of the icons, such as by hovering a mouse icon over an icon 1202, clicking an icon 1202, tapping an icon 1202 on a touch-sensitive screen, or by other entry methods, the web site 120 may be configured to bring up a new page, such as the page described with respect to FIG. 13.

The icons 1202 can be displayed in different ways to indicate various conditions of the sensor. For example, if the sensor senses a warning condition, the icon 1202 may be displayed in a different way from a normal condition. In one embodiment, the icons 1202 may be green if they measurements are within a normal range, but may be changed to yellow or red if the measurements indicate a warning or critical condition. Other than changing color to indicate condition, the icons 1202 can also be displayed in other ways, such as by changing the size or shape of the icon 1202, or by flashing the icon 1202, or other means of distinguishing an abnormal condition from a normal one.

The user interface 1200 may be configured to show different types of sensors. For example, if a client has any combination of pressure sensors, flow rate sensors, chlorine sensors, etc., each type of sensor may be displayed differently. As an example, the different types may be distinguished by using different colors (e.g., blue, green, black, etc.) for the icons. The different sensors may also be shown with icons of different shapes (e.g., circle, square, triangle, etc.).

Figure 13:
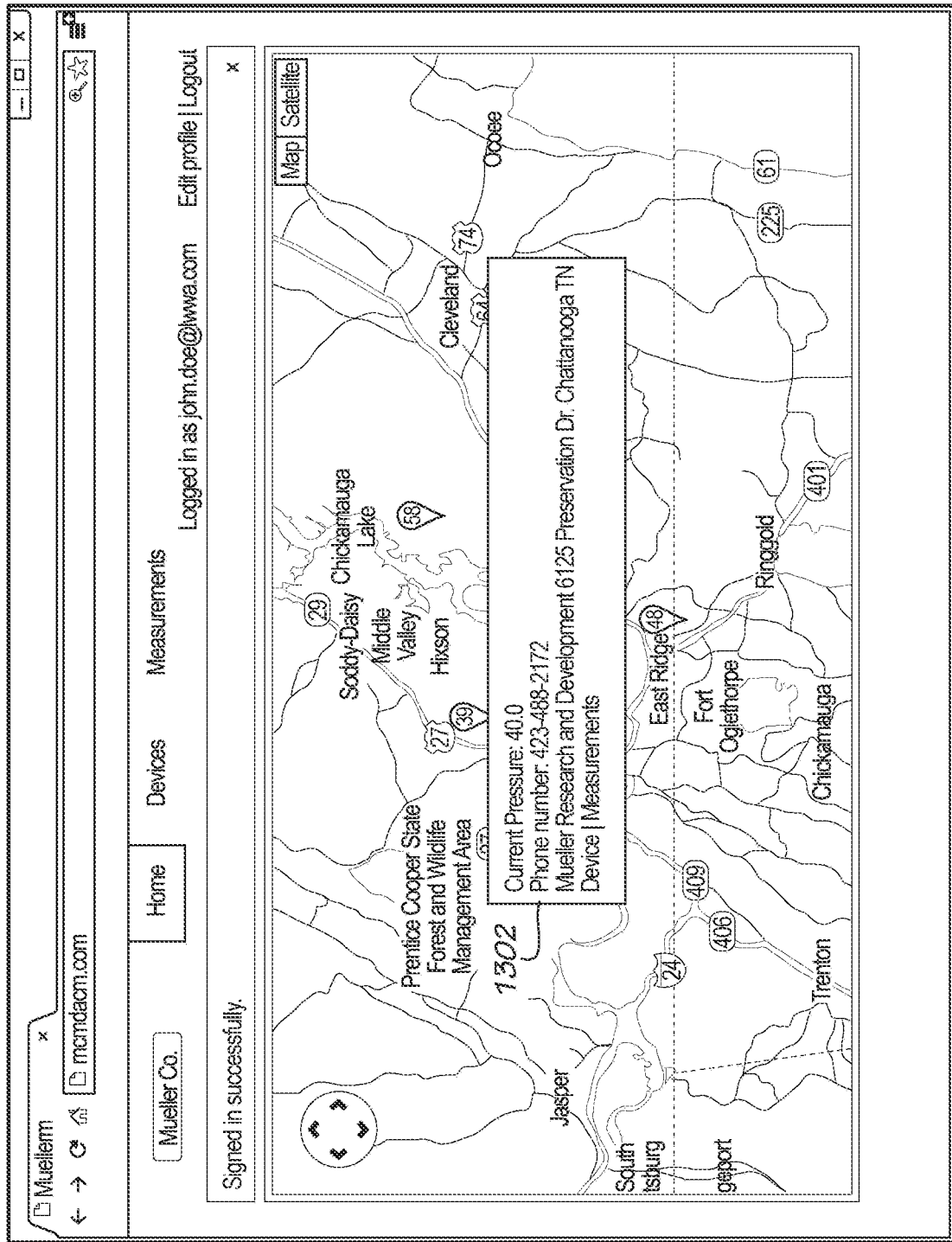
FIG. 13 is a screen view of a user interface showing the map of FIG. 12 with information about a sensing device superimposed, according to various embodiments of the present disclosure.

FIG. 13 is an example of a screen view of a web page that may be displayed on a user interface 1300 showing a map of sensing locations with information about a sensing device superimposed. In this example, the information for the selected sensor is displayed in a box 1302, representing a device condition window. The information may include a current reading for that sensor. With respect to implementations in which the sensing device is a pressure sensor, the reading may give a value in units of pounds per square inch (psi). The illustrated example shows a current pressure of 40.0 psi. If the sensor is configured to measure chlorine content, for instance, the box 1302 may display "Chlorine Content" with the reading.

If the reading (e.g., pressure) is out of a normal range, then the numbers may be highlighted in a particular way to draw attention to it. For example, the number may appear in yellow if the reading is within a warning level and may appear in red if it is within a critical condition. Also, green may be a color used to indicate that the reading is normal.

The box 1302 may also include a phone number of the device 102, which may be the cellular number used to communicate the data to the cellular network 116. The box 1302 may also include an address of the device 102.

Figure 14:
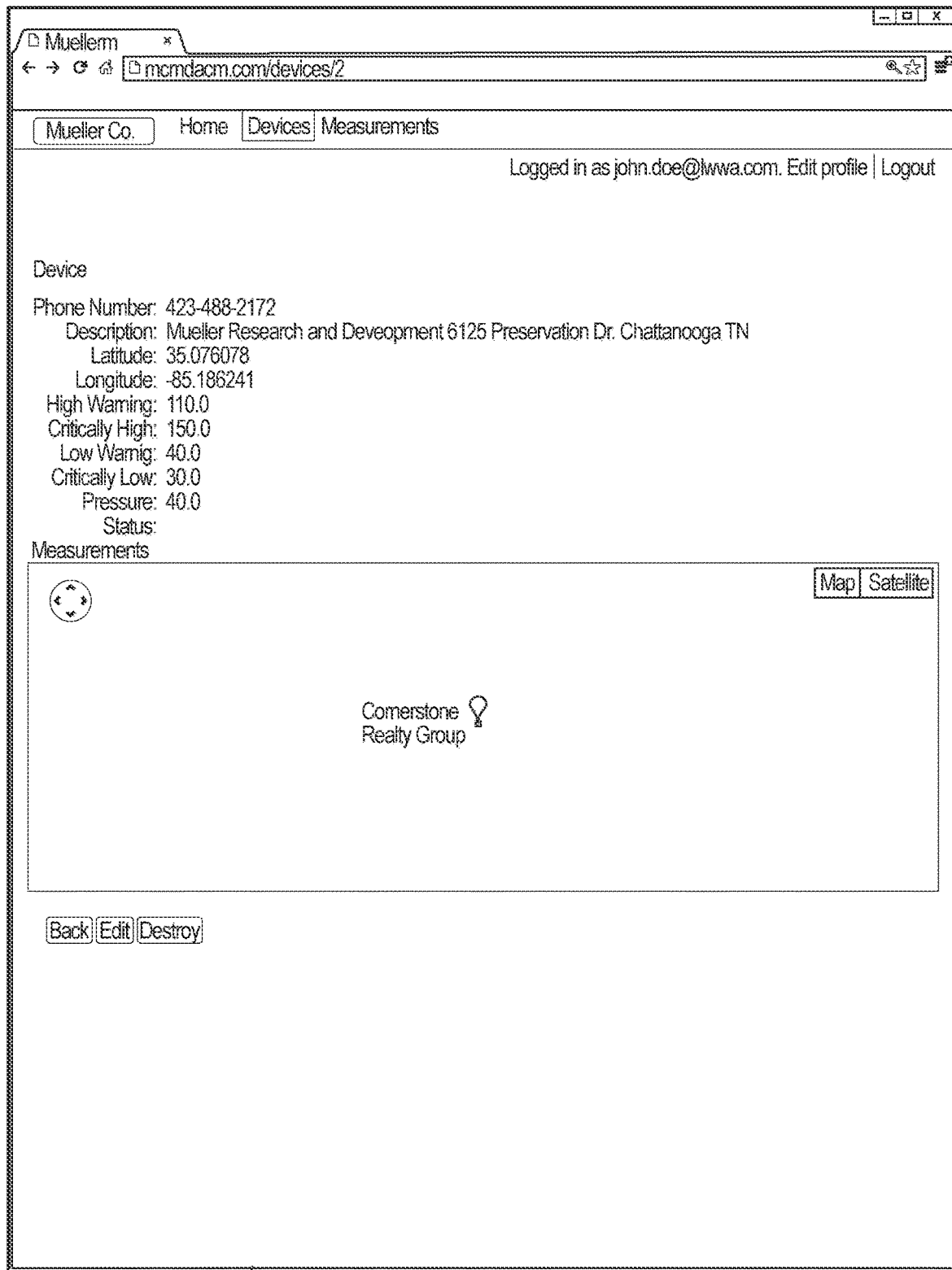
FIG. 14 is a screen view of a user interface showing further details of a sensing device, according to various embodiments of the present disclosure.

The superimposed box 1302 may also include a first link to "Device" and a second link to "Measurements." The first link allows a user to navigate to another web page, such as the web page described with respect to FIG. 14. The second link allows the user to navigate to yet another web page, such as the web page described with respect to FIG. 16.

FIG. 14 is an example of a screen view of a web page that may be displayed on a user interface 1400 showing further details of a sensing device. For example, this web page may be displayed when the user selects the "Devices" link shown in FIG. 13 or when the user navigates to the page by some other route. The user interface 1400 shows more details of the particular sensing device highlighted at an earlier time. The device information may include the phone number, a description of its location, latitude and longitude information, high warning level, critical high level, low warning level, and critical low level. The information may also include a reading of a particular property (e.g., pressure). The measurement value (e.g., pressure) may be highlighted in any suitable way if the value is outside of the range indicated by the high and low warning levels or outside the range indicated by the high and low critical condition levels.

The high warning level, critically high level, low warning level, and critically low level may be set by the client, having an understanding of the nature of the various pipes throughout the water distribution system. For example, a high warning level of 110.0 psi is a level that the client knows may be an indication of a problem that should likely be investigated. A critically high level of 150.0 psi is likely an indication that a pipe is about to burst. A low warning level of 40.0 psi may indicate a small leak in the pipe, and a critically low level of 30.0 psi may indicate a larger leak that likely needs to be attended to immediately. Also, when a critically low level occurs in a pressure reading, the client may need to notify its customers of a "boil" notice that water may be engraphed with contaminates.

A "status" output may also be displayed. If status is normal, the output may be blank, but if the status is a warning or critical, the status indication may be changed to show such conditions. For example, the status may change to a different color, may blink, or may include some other type of highlighting feature. In one embodiment, for a warning, the status output may be displayed yellow, and for a critical condition, the status output may be displayed red.

Figure 15:
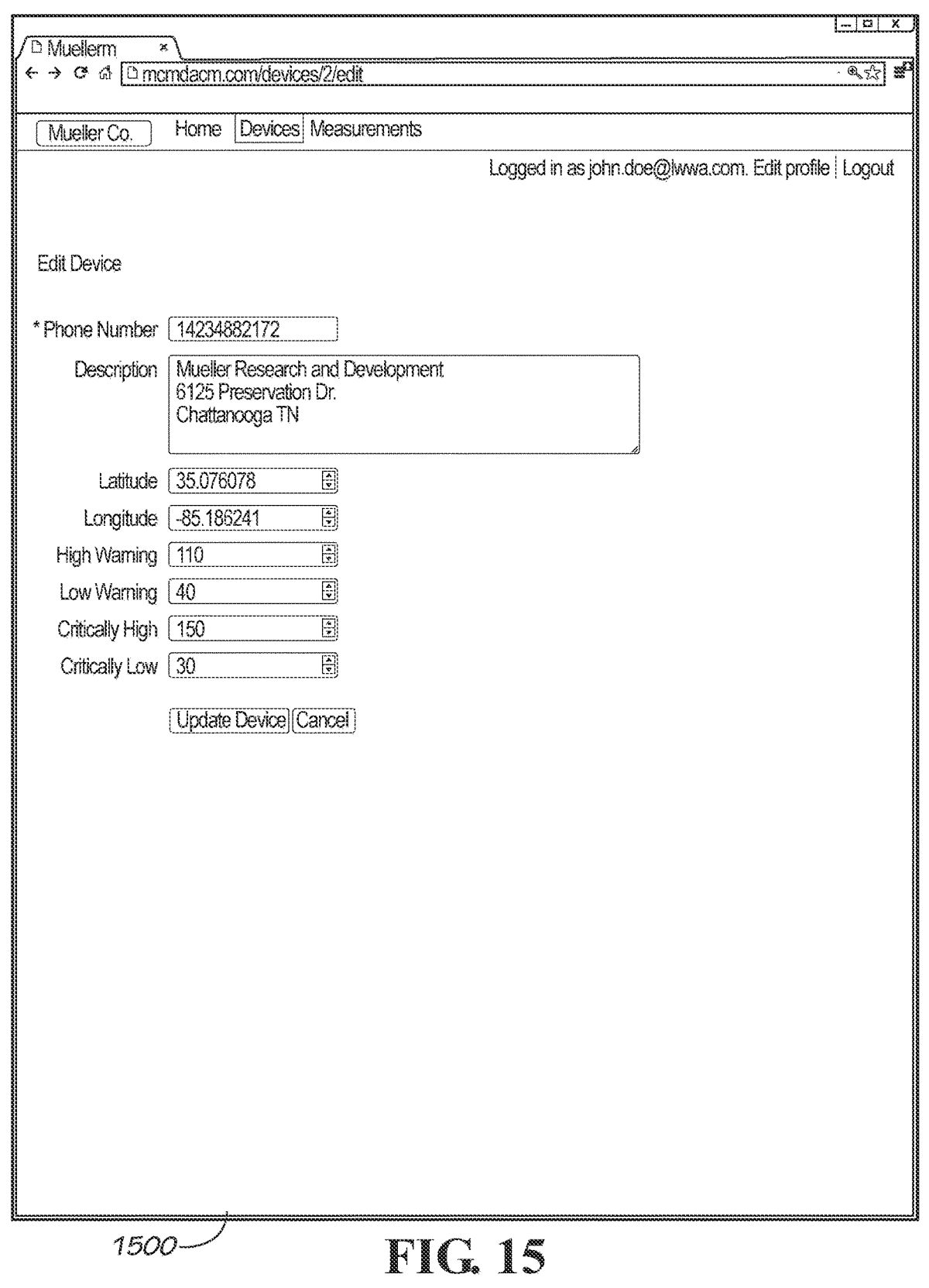

FIG. 15 is an example of a screen view of a web page that may be displayed on a user interface 1500 for enabling a user to edit parameters of a sensing device. In this web page, the user can change the description, which may include location information of the device. The user can also change the latitude and longitude information, and the high and low warning and critical condition levels. When finished editing, the user can click on the "update device" button. In some embodiments, the phone number box may not be available to the client but may only be available for users of the management company.

Figure 16:
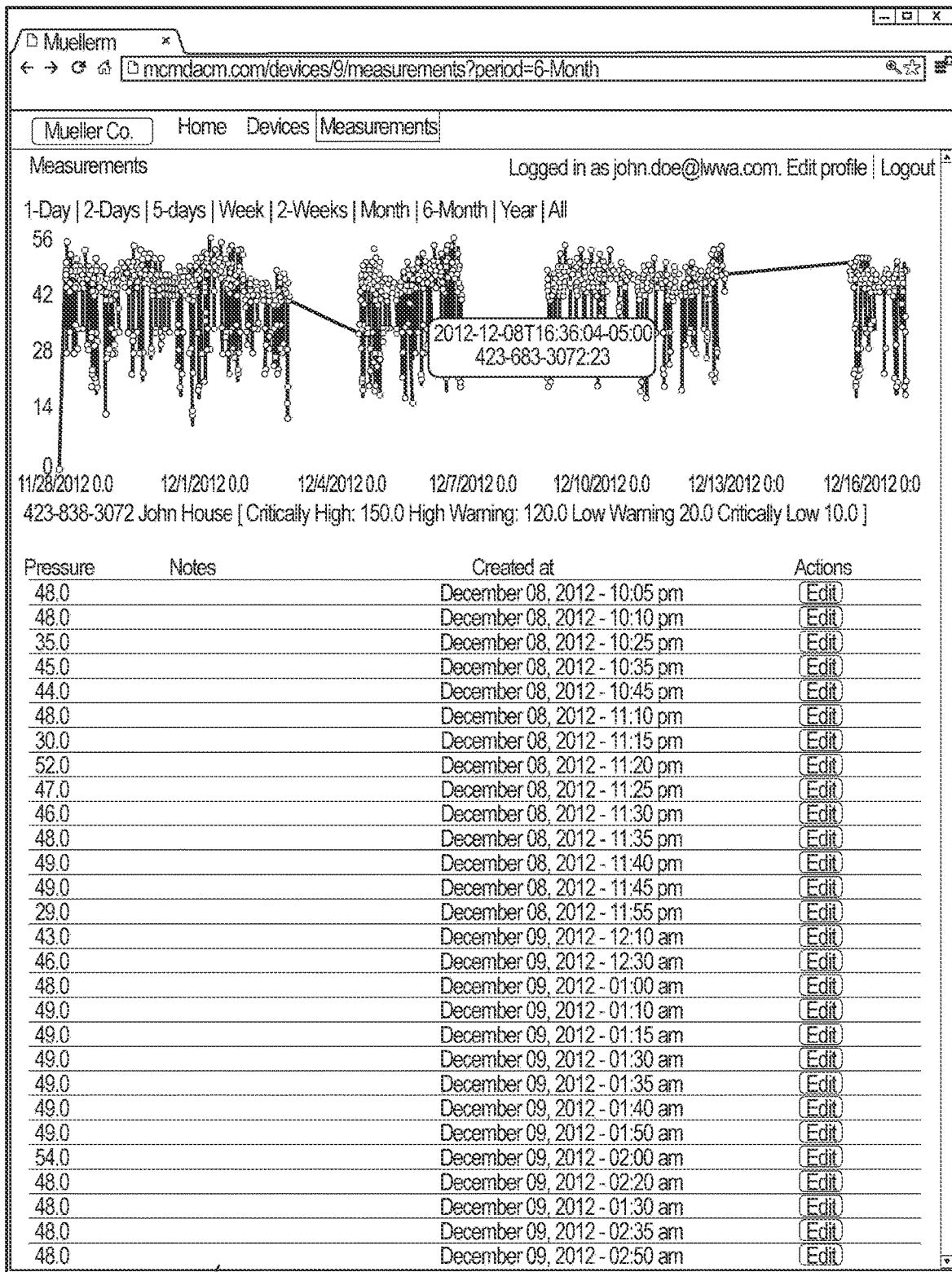
FIG. 16 is a screen view of a user interface showing a graph and a table of measurements logged by a sensing device, according to various embodiments of the present disclosure.

FIG. 16 is an example of a screen view of a web page that may be displayed on a user interface 1600 showing a graph and data points representing measurements by a sensing device. This web page shows measurement data from one sensor over certain time periods. The user may select time periods of 1 day, 2 days, 5 days, 1 week, 2 weeks, 1 month, 6 months, 1 year, or all. The graph section of the web page shows the high and low points for each day. The data point section shows the reading (e.g., pressure), notes (if any), and the time when the measurement was taken. This web page also gives the user an option to edit or annotate a particular record by pressing the "edit" button on the same line as the record.

The data points in the graph and in the table may be highlighted in any suitable way to indicate when a measurement is outside a range of normal limits. For example, the date points or measurement readings may be given a different color, size, shape, or other distinctive feature to indicate abnormal conditions.

Figure 17:
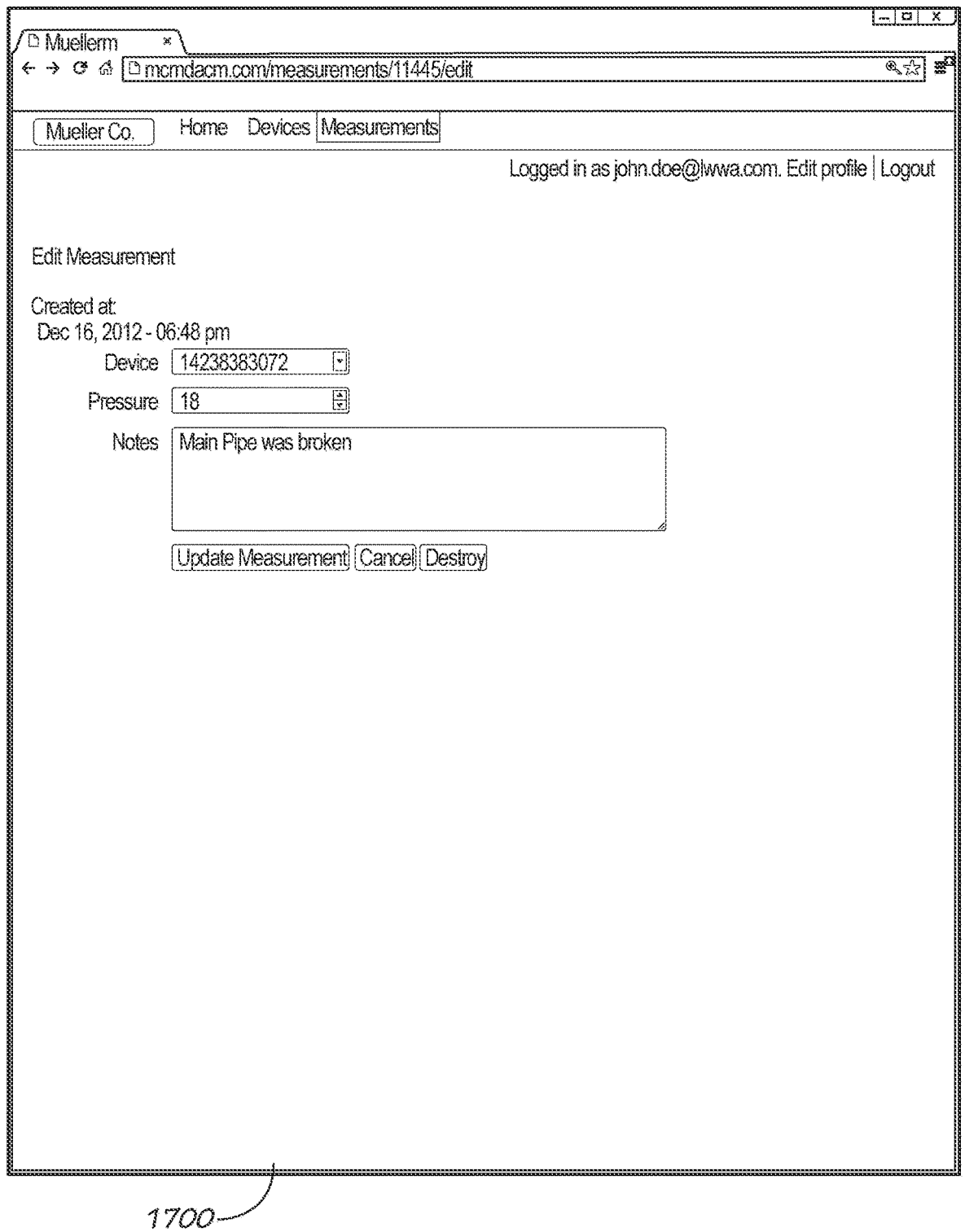
FIG. 17 is a screen view of a user interface for enabling a user to edit measurements, according to various embodiments of the present disclosure.

FIG. 17 is an example of a screen view of a web page that may be displayed on a user interface 1700 for enabling a user to edit measurements. For example, if the user of the user interface 1600 of FIG. 16 presses the "edit" button, the web site 120 navigates the user to the user interface 1700. In this page, the user can enter a note that is saved with the particular data record. In this example, the user wishes to annotate a low pressure reading that occurred when the client was aware that a pipe was broken. In this case, the user enters a message, such as "Main Pipe was broken." To enter the new note into the database 122, the user selects the "update measurement" button. In some embodiments, the "destroy" button may not be available or may be available to a limited extent. The purpose of the destroy button is to remove the particular sensor from the system and/or ignore any readings or communications from the sensor.

Figure 18:
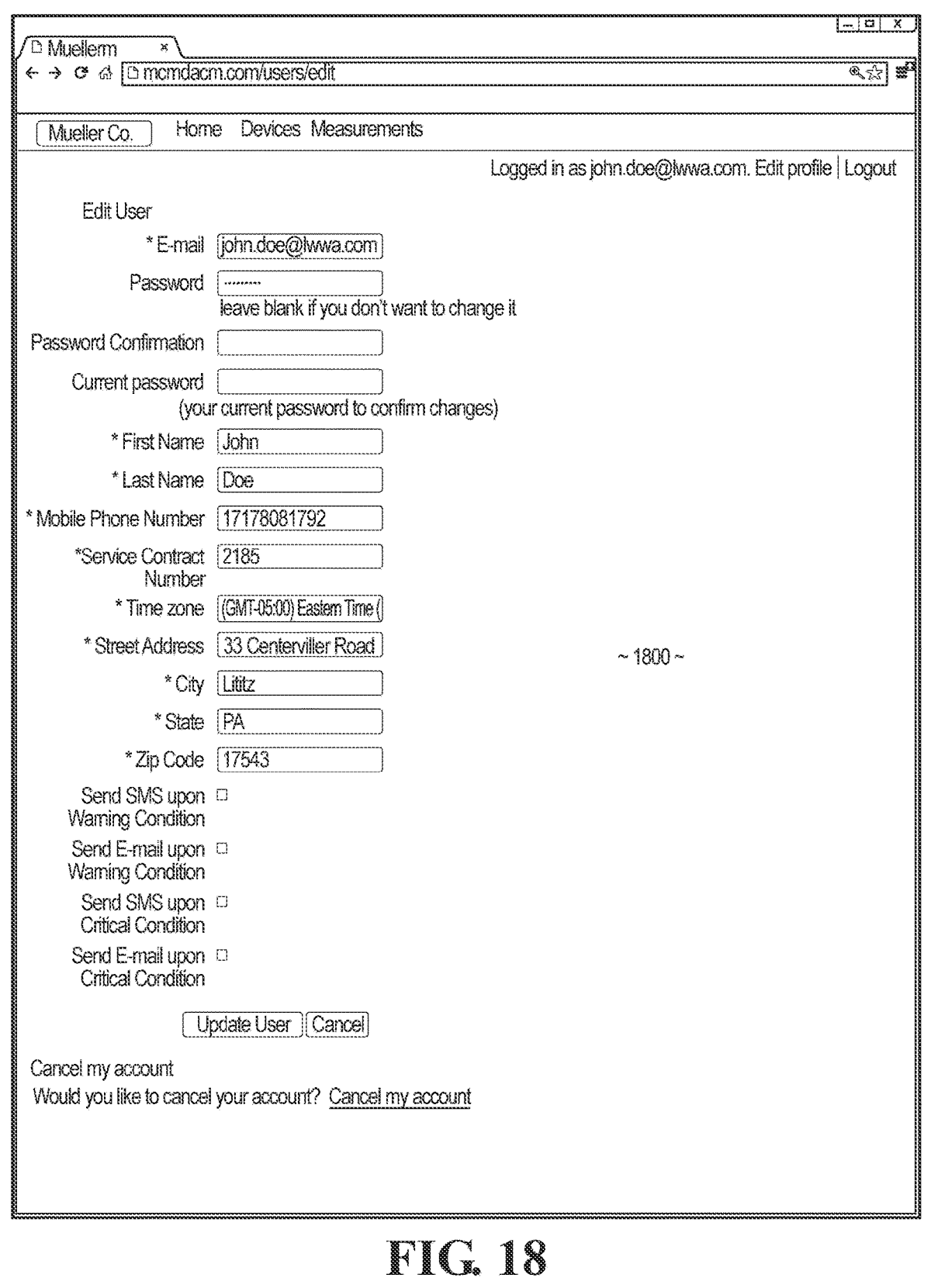

FIG. 18 is an example of a screen view of a web page that may be displayed on a user interface 1800 for enabling a user to edit user information. The user interface 1800 in this example is similar to the user sign-up page shown in FIG. 11. A user can access this page using the "Edit Profile" link on any of the user interfaces shown in FIGS. 12-18. The user can edit any information, such as e-mail, address, password, or other personal information. The user can also edit the ways that the user will receive warnings from the system 100. For example, if the user decides that he or she wants to receive both an SMS message and an e-mail when there is a critical condition, the user can check the appropriate boxes.

The server 160 may be part of the utility company (e.g., water utility company) and provide communication with other users via the communication network. In some embodiments, the server may be part of a company responsible for managing the utility measurement data. The communication network in these embodiments may be a local area network (LAN), wide area network (WAN), such as the Internet, or any other suitable data communication networks. The communication network may also include other types of networks, such as plain old telephone service (POTS), cellular systems, satellite systems, etc.

The server 160 may detect extreme events and provide an alarm in response. The alarm may be in the form of an automated e-mail, a pop-up window, an interrupt signal or indication on a computer of the client device 162, SMS, or other suitable message signifying an urgent event.

The client system 106 may include a computer system used by the utility provider. In this respect, the utility provider system may be a client of the data management company that manages the utility measurement data and/or provides monitoring services regarding the status of the utility infrastructure. The client system, therefore, may be able to receive and review status updates regarding the infrastructure. Alarms may be provided to the client system, which may then be acknowledged and confirmed. The client system may also receive historic data and manage the client's accounts and usage information. In some embodiments, information may be provided to the client system in a read-only manner.

The sensing devices 152 and client devices 162 may communicate with the server 160 by a cellular service, via cellular towers and/or satellites. The wireless communication between the devices may be active during some periods of time (when two respective devices are linked) and may be inactive during other periods of time (when the devices are not linked and/or are in sleep mode). Alternatively, any of the sensing devices 152 may be connected to the network 156 through wired connections.

The water mains may include transmission mains, which may include water pipes having an inside diameter of at least twelve inches. The water mains also include distribution mains, which may include smaller pipes having an inside diameter of less than twelve inches. The transmission mains, having a greater size, may be configured to allow a greater amount of water flow in comparison with the distribution mains. The transmission mains may be located nearer to the utility source and the distribution mains may be located farther from the utility provider. In some systems, distribution mains may be located along secondary roads or residential roads.

The cellular network 116 may include relay devices (e.g., using ISM frequency transmission) for relaying radio signals from the cell towers 154 to the data network 156. The network 156 in some embodiments may also include the cellular network 116, a satellite network, a radio network, a LAN, a WAN, or any other suitable network.

In some embodiments, the sensing devices 152 may comprise printed circuit board with the components of a sensor interface, processing device, and communication device incorporated on the printed circuit board. In other embodiments, multiple printed circuit boards may be used with the components of the sensor interface, processing device, and communication device incorporated on the boards in any suitable configuration. When the electrical components are disposed on multiple boards, standoffs may be used as needed. Connectors may be used to couple the processing device with the sensor interface and communication device.

The sensor assembly may include any combination of sensors for detecting various parameters that may be analyzed. For example, the sensor assembly may include one or more piezoelectric sensors, acoustic sensors, acoustic transducers, hydrophones, pressure sensors, pressure transducers, temperature sensors, accelerometers, flow sensors, chlorine sensors, leak detectors, vibration sensors, or other types of sensors.

The power supply of the sensor assembly may contain one or more batteries, solar-powered devices, electrical power line couplers, or other power sources. When external power is received, additional connectors or ports may be added through the walls of the enclosure. When batteries are used, the power supply may also include a battery capacity detection module for detecting the capacity of the one or more batteries. In some embodiments, the power may be partially or completely supplied by the energy harvesting device housed on the sensor assembly itself.

A sensor interface may be incorporated in the sensor assembly. The sensor interface may be configured to acquire the acoustic, pressure, and/or temperature data from the sensor assembly. In addition, the sensor interface may include amplification circuitry for amplifying the sensed signals. The sensor interface may also include summing devices, low pass filters, high pass filters, and other circuitry for preparing the signals for the processing device. The sensor assembly may also include a processing device configured to log the measurement information and save it in memory until a designated upload time or when requested by a client.

The communication device of the sensor assembly may include a modem, such as a cellular or ISM-enabled modem to provide network access to the communication device. Also, the communication device may include a tuning module, such as a GPS timing receiver, for providing an accurate timing reference and for synchronizing timing signals with other elements of the cellular network 116. The communication device may be configured to transmit and receive RF signals (e.g., ISM frequency signals), cellular signals, GPS signals, etc., via the antenna 114.

The processing device housed in the sensor assembly may include a processor, a sensor data handling device, a power assembly, a communication module, a time/sleep module, a data processing module, a health status detecting module, and a storage module. The processor may comprise one or more of a microcontroller unit (MCU), a digital signal processor (DSP), and other processing elements.

The sensor data handling device connects with the sensor interface and handles the sensor data to allow processing of the signals by the processor. The power assembly may comprise a power source, which may be separate from the power supply. In some embodiments, however, the power assembly may be connected to the power supply. The power assembly may also be configured to control the voltage and current levels to provide constant power to the processor. In some embodiments, the processor may be provided with about 3.3 volts DC. The communication module connects with the communication device and receives and/or sends signals for communication through the communication device. In some embodiments, the communication device may include a GPS device for receiving timing samples for synchronization purposes. The timing samples may be forwarded to the communication module to allow the processing device to be synchronized with other devices. The timing samples may also be used to wake up the processing device when needed or sleep when inactive.

The processing device also includes a time/sleep module for providing timing signals to the processor and may include a crystal oscillator. The time/sleep module also controls sleep modes in order to minimize battery usage when the sensor assembly is not in use. For example, the processor may include an MCU that operates continually and a DSP that sleeps when not in use. Since the DSP normally uses more power, it is allowed to sleep in order to conserve battery power.

The time/sleep module may be configured to wake various components of the processor at designated times in order that sensor data stored during a previous time may be transmitted to the host. In some embodiments, the time/sleep module may wake the sensor assembly at a certain time during the day, enable the sensor assembly to analyze and record the measurements, return to a sleep mode according to the sampling rate, and repeat the analysis every 15 seconds or so for about 15 minutes. At the end of log period, the communication device sends the data to the server 160 and the time/sleep module returns the device to a sleep mode until the next designated time. Separate from the regular sensing schedule, the time/sleep module may be configured to wake up the processor in the event that a warning or critical condition has been detected.

The storage module of the sensor assembly may include flash memory, read-only memory (ROM), random access memory (RAM), or other types of memory.

Pressure sensors may be used in particular to measure an absolute pressure value. Also, pressure sensors may be used as a burst sensor. In this respect, the sensor may measure a high-speed pressure transient profile. Both the pressure change value and absolute pressure value may be useful for different applications. The sensor(s) may measure voltage signals or frequency measurements. Temperature sensors may also be used for measuring the temperature of the pipe. The sensed waveform signals are supplied to the processing device, which may process the signals at the point of measurement. In other embodiments, the signals may be transmitted to the host for processing.

It should be noted that the functions of the sensor assembly may be configured in software or firmware and the functions performed by the processor. The processor, as mentioned above, may include a DSP, microcontroller, or other types of processing units. In some embodiments, the signals may be communicated to the server 160 where processing may occur. The real time processing may be performed by a DSP, for example.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

The invention claimed is:

1. A water sensing assembly comprising:
   a housing mountable on a water pipe;
   a sensor configured to be exposed to water flow within the water pipe;
   a generator positioned within the housing;
   a battery pack comprising a rechargeable battery; and
   a vertical axis turbine coupled to a generator shaft of the generator and positionable through a bore in the water pipe into the water flow within the water pipe, an axis of the turbine aligned with an axis of the generator shaft of the generator, the generator configured to generate an electrical current from rotation of the turbine by the water flow for recharging of the battery pack, the water sensing assembly thereby configured to recharge itself before full depletion of the battery pack.

2. The water sensing assembly of claim 1, wherein the turbine is indirectly coupled to the generator, the turbine positioned outside a sealed interior of the housing.

3. The water sensing assembly of claim 2, wherein the turbine is indirectly coupled to the generator through magnets.

4. The water sensing assembly of claim 2, wherein the sealed interior of the housing is sealed with a seal partition, a turbine shaft of the turbine extending through the seal partition.

5. The water sensing assembly of claim 1, further comprising:
   measurement and communications electronics connected to the sensor; and
   an antenna connected to the measurement and communications electronics.

6. The water sensing assembly of claim 1, wherein the sensor is a pressure sensor.

7. The water sensing assembly of claim 6, wherein the sensor is between the turbine and the generator.

8. The water sensing assembly of claim 1, wherein the turbine defines a turbine axis and comprises two wings, each wing defining a curved profile and extending in opposite spirals on either side of the turbine axis.

9. The water sensing assembly of claim 1, further comprising a housing, a mounting bracket attached to the housing, a port bracket, and an insertion screw connecting the mounting bracket to the port bracket, the insertion screw configured to insert the turbine into the water pipe by pulling the mounting bracket towards the port bracket when the insertion screw is tightened.

10. The water sensing assembly of claim 1, wherein the turbine extends beyond the housing.

11. The water sensing assembly of claim 1, further comprising an antenna, the antenna in electrical communication with and thereby powered by the battery pack.

12. The water sensing assembly of claim 1, further comprising measurement and communication electronics, the measurement and communication electronics in electrical communication with and thereby powered by the battery pack.

13. The water sensing assembly of claim 1, further comprising an antenna, a battery pack, and measurement and communication electronics, each of the antenna and the measurement and communication electronics in electrical communication with and thereby powered by the battery pack.

14. A water sensing assembly comprising:
a housing mountable on a water pipe;
a sensor configured to be exposed to water flow within the water pipe;
a generator; and
a battery pack, wherein the housing encloses at least one of the sensor, the generator, and the battery pack; and
a vertical axis turbine coupled to a generator shaft of the generator and positionable through a bore in the water pipe into the water flow within the water pipe, an axis of the turbine aligned with an axis of the generator shaft of the generator, the generator configured to generate an electrical current from rotation of the turbine by the water flow for recharging of the battery pack, the water sensing assembly thereby configured to recharge itself before full depletion of the battery pack.

15. The water sensing assembly of claim 14, wherein the turbine extends beyond the housing.

16. The water sensing assembly of claim 14, further comprising an antenna, a battery pack, and measurement and communication electronics, each of the antenna and the measurement and communication electronics in electrical communication with and thereby powered by the battery pack.

* * * * *